US005738989A

United States Patent [19]
Kohne

[11] Patent Number: 5,738,989
[45] Date of Patent: Apr. 14, 1998

[54] METHOD FOR DETERMINING THE SENSITIVITY OF MICROORGANISMS TO ANTI MICROBIAL AGENTS USING RIBOSOMAL NUCLEIC ACID HYBRIDIZATION

[75] Inventor: David E. Kohne, La Jolla, Calif.

[73] Assignee: Gen-Probe Incorporated, San Diego, Calif.

[21] Appl. No.: 460,124

[22] Filed: Jun. 2, 1995

Related U.S. Application Data

[62] Division of Ser. No. 199,486, Feb. 22, 1994, which is a continuation of Ser. No. 179,922, Jan. 11, 1994, abandoned, which is a continuation of Ser. No. 857,081, Mar. 19, 1992, Pat. No. 5,288,611, which is a continuation of Ser. No. 584,432, Sep. 12, 1990, abandoned, which is a continuation of Ser. No. 464,717, Jan. 12, 1990, abandoned, which is a continuation of Ser. No. 353,208, May 17, 1989, abandoned, which is a continuation of Ser. No. 655,365, Sep. 4, 1984, abandoned, which is a continuation-in-part of Ser. No. 456,729, Jan. 10, 1983, abandoned.

[51] Int. Cl.$^6$ .................................................. C12Q 1/68
[52] U.S. Cl. ............................ 435/6; 935/77; 935/78
[58] Field of Search .............................. 435/5, 6, 32, 7.2

[56] References Cited

U.S. PATENT DOCUMENTS

| | | | |
|---|---|---|---|
| 3,755,086 | 8/1973 | Heimer | 435/6 |
| 3,930,956 | 1/1976 | Juni | 435/6 |
| 4,033,143 | 7/1977 | Juni | 435/6 |
| 4,228,238 | 10/1980 | Swanson | 435/6 |
| 4,237,224 | 12/1980 | Cohen et al. | 435/6 |
| 4,275,149 | 6/1981 | Litman et al. | 435/6 |
| 4,302,204 | 11/1981 | Wahl et al. | 435/6 |
| 4,358,535 | 11/1982 | Falkow et al. | 435/6 |
| 4,394,443 | 7/1983 | Weissman et al. | 435/6 |
| 4,416,988 | 11/1983 | Rubin | 435/6 |
| 4,480,040 | 10/1984 | Owens et al. | 435/6 |
| 4,677,054 | 6/1987 | White et al. | 435/6 |
| 4,717,653 | 1/1988 | Webster | 435/6 |
| 4,851,330 | 7/1989 | Kohne | 435/6 |
| 5,087,558 | 2/1992 | Webster | 435/6 |
| 5,288,611 | 2/1994 | Kohne | 435/6 |
| 5,348,854 | 9/1994 | Webster | 435/6 |

FOREIGN PATENT DOCUMENTS

| | | |
|---|---|---|
| 0155359 | 9/1982 | European Pat. Off. |
| 0079139 | 10/1982 | European Pat. Off. |
| 0120658 | 3/1984 | European Pat. Off. |
| 0133671 | 7/1984 | European Pat. Off. |
| 0155360 | 12/1988 | European Pat. Off. |
| 8301073 | 3/1983 | WIPO |
| 8401174 | 3/1984 | WIPO |
| 8402721 | 7/1984 | WIPO |

OTHER PUBLICATIONS

Abou–Sabe and Pilla, "Transposition of the D-Ribose Operon of *E. coli* B/r," *Abstract of the Annual Meeting of the American Society for Microbiology* (1981), Rutgers University, New Brunswick, N.J.

Agarwal et al., "Total Synthesis of the Gene for an Alanine Transfer Ribonucleic Acid from Yeast," *Nature*, 227:27–34 (1970).

Alwine et al., "Method for Detection of Specific RNAs in Agarose Gels by Transfer To Diazobenzyloxymethyl–Paper and Hybridization with DNA Probes," *Proc. Natl. Acad. Sci. USA* 74:5350–5354 (1977).

Amikam et al., "Mycoplasmas (Mollicutes) Have a Low Number of rRNA Genes," *Journal of Bacteriology* 158:376–378 (1984).

Amikam et al., "Ribosomal RNA genes in Mycoplasma," *Nucleic Acids Research* 10:4215–4222 (1982).

Bahareen et al., "Complementary DNA — 25S ribosomal RNA hybridization: an improved method for phylogenetic studies," *Can. J. Microbiol.* 29:546–551 (1983).

Baharaeen, "The evolution of antarctic yeasts," *Ph.D. Thesis: Oklahoma State University; Diss. Abs. Int.* 43/10B:3138–3297 (1982).

Bailey and Scott, *Diagnostic Microbiology*, 4th ed. (St. Louis: The C.V. Mosby Company, 1974) 327–328.

Baker et al., "Delayed Hypersensitivity Reactions Provoked by Ribosomes from Acid–Fast Bacilli," *Infection and Immunity* 6:258–265 (1972).

Baker et al., "Ribosomes of Acid–Fast Bacilli: Immunogenicity Serology, and In Vitro Correlates of Delayed Hypersensitivity," *Infection and Immunity* 8:236–244 (1973).

Balch et al., "An Ancient Divergence among the Bacteria," *J. Mol. Evol.* 9:305–311 (1977).

Balch et al., "Methanogens: Reevaluation of a Unique Biological Group," *Microbiological Reviews* 43:260–296 (1979).

(List continued on next page.)

*Primary Examiner*—Lisa B. Arthur
*Attorney, Agent, or Firm*—Lyon & Lyon LLP

[57] ABSTRACT

A method for detecting and quantitating organisms containing R-RNA, t-RNA, other RNA, any member of a large, intermediate or small category of organisms such as any member of a bacterial taxonomic Family, Genus, or Species, and previously unknown organisms. The method comprises contacting the nucleic acid of the organisms whose presence, identification and quantitation are to be determined, with a marked probe comprising nucleic acid molecules complementary to RNA or other nucleic acid sequences, of the said organism, under nucleic acid hybridization conditions, and then determining the degree of hybridization that has occurred. The method may include contacting a sample with an enzyme-detergent mixture to make the nucleic acids of the organism or virus in a sample more readily available for hybridization. The method can also be used to determine the sensitivity of particular groups of organisms to antimicrobial agents, to determine the presence of substances with antimicrobial activity, and to determine the state of growth of microorganisms and other cells.

62 Claims, No Drawings

OTHER PUBLICATIONS

Barry et al., "The 16s/23s Ribosomal Spacer Region as a Target for DNA Probes to Identify Eubacteria," *PCR Methods and Application* 81:51–56 (1991).

Baumlein et al., "The Basic Repeat Unit of a *Chlronomus balbiani* Ring Gene," *Nucleic Acid Research* 10:3893–3904 (1982).

Bendich and McCarthy, "Ribosomal RNA Homologies among Distantly Related Organisms," *Proc. Natl. Acad. Sci.* 65:349–356 (1970).

Bicknell and Douglas, "Nucleic Acid Homologies Among Species of Saccharomyces," *Journal of Bacteriology* 101:505–512 (1970).

Blair et al., "Unfolded 30 S Ribosomal Subunits," *Biophysical Chemistry* 14:81–89 (1981).

Bohnert et al., "Homologies Among Ribosomal RNA and Messenger RNA Genes in Chloroplasts, Mitochondria and *E. coli*," *Molecular Gene Genetics* 179:539–545 (1980).

Bonen et al., "Cyanobacterial evolution: results of 16S ribosomal ribonucleic acid sequence analysis," *Can. J. Biochem.* 57:879–888 (1979).

Borras et al., "Inability to Transmit Scrapie by Transfection of Mouse Embryo Cells in vitro," *J. Gen. Virol.* 58:263–271 (1982).

Brenner et al., "Batch Procedure for Thermal Elution of DNA from Hydroxyapatite," *Anal. Biochem.* 28:447–459 (1969).

Brenner et al., "Conservation of Transfer Ribonucleic Acid and 5S Ribonucleic Acid Cistrons in Enterobacteriaceae" *Journal of Bacteriology* 129:1435–1439 (1977).

Brenner, "Deoxyribonucleic Acid Reassociation in the Taxonomy of Enteric Bacteria," *Int. J. Systematic Bacteriology* 23:298–307 (1973).

Brenner and Falkow, "Molecular Relationships Among Members of The Enterobacteriaceae," *Advances in Genetics* 16:81–118 (1971).

Britten et al., "Analysis of Repeating DNA Sequences by Reassociation," *Methods in Enzymology* eds. Grossman and Moldave (Academic Press:NY 1974) Ch. 29, pp. 363–419.

Britten and Kohne, "Implications of repeated nucleotide sequences," in *Handbook of Molecular Cytology*, ed. A. Neuberger and E.L. Tatum (North–Holland Publishing Co.: Amsterdam, 1969) vol. 15, pp. 38–51.

Britten and Kohne, "Repetition of nucleotide sequences in chromosomal DNA," in *Handbook of Molecular Cytology*, ed. A. Neuberger and E.L. Tatum (North–Holland Publishing Co.: Amsterdam, 1969) vol. 15, pp. 22–36.

Britten and Kohne, "Repeated Segments of DNA," *Sci. Amer.* 222:24–31 (1970).

Britten and Kohne, "Repeated Sequences in DNA," *Science* 161:529–540 (1968).

Brooks, "Calbiochem® Hydroxylapatite," Calbiochem® Brand Biochemicals Behring Diagnostics, Div. of American Hoechst Corp., pp. 3–32 (1981).

Brooks et al., "Red Pigmented Micrococci: a Basis for Taxonomy," *Intl. J. Syst. Bacteriol.* 30:627–646 (1980).

Brown et al., "Chemical Disinfection of Creutzfeldt–Jakob Disease Virus," *New England Journal of Medicine* 306:1279–1282 (1982).

Byers et al., "Presence of Virus-specific DNA Sequences in Murine Type C Viruses," *J. gen. Virol.* 43:611–621 (1979).

Carbon et al., The sequence of the 16S RNA from Proteins vulgaris. Sequence comparison with *E. coli* 16S RNA and its use in secondary structure model building, *Nucleic Acids Research* 9:2325–2333 (1981).

Casey and Davidson, "Rates of formation and thermal stabilities of RNA:DNA and DNA:DNA duplexes at high concentrations of formamide," *Nucleic Acids Research* 4:1539–1552 (1977).

Chattopadhyay et al., "Ribosomal RNA Genes of Neurospora: Isolation and Characterization," *Proc. Natl. Acad. Sci. USA* 69:3256–3259 (1972).

Chung et al., "Characterization of the histone core complex," *Proc. Natl. Acad. Sci. USA* 75:1680–1684 (1978).

Conner et al., "Detection of sickle cell $\beta^S$-globin allele by hybridization with synthetic oligonucleotides," *Proc. Natl. Acad. Sci. USA* 80:278–282 (1983).

Cox and Kelly, "Structural Aspects of Eukaryotic Ribosomes," *Biochem. Soc. Symp.* 47:11–48 (1982).

Cox and Thompson, "Distribution of Sequences common to the 25–28S–Ribonucleic Acid Genes of *Xenopus laevis* and *Neurospora crassa*," *Biochem. J.* 187:75–90 (1980).

Cunningham, "Spot Blot: A Hybridization Assay for Specific DNA Sequences in Multiple Samples," *Analytical Biochemistry* 128:415–421 (1983).

Curtis, "Studies on the nuclear genome of *Euglena gracilis*," *Diss. Abs. Int.* 41:3683 (1981).

Daniell et al., "Characterization of the Inhomogeneous DNA in Virions of Bacteriophage Mu by DNA Reannealing Kinetics," *Journal of Virology* 15:739–743 (1975).

Daubert and Dahmus, "Synthesis and characterization of a DNA probe complementary to rat liver 28S ribosomal RNA," *Biochem. and Biophys. Res. Comm.* 68:1037–1044 (1976).

De Ley, "Modern Molecular Methods in Bacterial Taxonomy: Evaluation Application, Prospects", *Proc. 4th Int. Conf. Plant. Path. Bact.–Angers*, 347–357 (1978).

De Ley and De Smedt, "Improvements of the membrane filter method for DNA:rRNA hybridization," *Antonie van Leeuwenhoek* 41:287–307 (1975).

De Ley et al, "Intra–and intergeneric similarities of Chromobacterium and Janthinobacterium ribosomal ribonucleic acid cistrons," *Inter. J. Syst. Bact.* 28:154–168 (1978).

De Smedt and De Ley, "Intra–and Intergeneric Similarities of Agrobacterium Ribosomal Ribonucleic Acid Cistrons," *Intl. J. Syst. Bacteriol.* 27:222–240 (1977).

De Smedt et al., "Intra–and Intergeneric Similarities of Ribosomal Ribonucleic Acid Cistrons of Free–Living, Nitrogn–Fixing Bacteria," *Intl. J. Syst. Bacteriol.* 30:106–122 (1980).

Deisseroth et al., "Extinction of globin gene expression in human fibroblastxmouse erythroleukemia cell hybrids", *Somatic Cell Genetics* 2:373 (1976).

Doi and Igarashi, "Conservation of Ribosomal and Messenger Ribonucleic Acid Cistrons in Bacillus Species," *Journal of Bacteriology* 90:384–390 (1965).

Doi and Igarashi, "Heterogeneity of the Conserved Ribosomal RNA Sequences of *Bacillus subtilis*," *Journal of Bacteriology* 92:88–96 (1966).

Doolittle and Pace, "Transcriptional Organization of the Ribosomal RNA Cistrons in *Escherichia coli*," *Proc. Natl. Acad. Sci. USA* 68:1786–1790 (1971).

Dubnau et al., "Gene Conservation in Bacillus Species, I. Conserved Genetic and Nucleic Acid Base Sequence Homologies," *Genetics* 54:491–498 (1965).

Dunn and Hassell, "A Novel Method to Map Transcripts: Evidence for Homology between an Adenovirus mRNA and Discrete Multiple Regions of the Viral Genome," *Cell* 12:23–36 (1977).

Dunn and Sambrook, "Mapping Viral mRNAs by Sandwich Hybridization," *Methods in Enzymology* 65:468–478 (1980).

Eckhardt and Lürhmann, "Blocking of the Initiation of Protein Biosynthesis by a Pentanucleotide Complementary to the 3' End of *Escherichia coli* 16S rRNA," *J. Biol. Chem.* 254:11185–11188 (1979).

Finegold and Martin eds., "Diagnostic Microbiology," (C.V. Mosby Company:St. Louis, 1982) Sixth Edition.

Flavell et al., "DNA–DNA Hybridization on Nitrocellulose Filters: 1. General Considerations and Non–Ideal Kinetics," *Eur. J. Biochem.* 47:535–543 (1974).

Fox, "Archaebacterial 5S Ribosomal RNA," *Zbl. Bakt. Hyg. J. Abt. Orig.* C3:330–345 (1982).

Fox, "Archaebacteria, Ribosomes and the Origin of Eucaryotic Cells in *Evolution Today*," *Proc. 2nd Intl. Congr. of Syst. and Evol. Biol.,* Scudder and Reveal, eds., (Univ. Maryland Press, 1981) pp. 235–244.

Fox, "Insights into the Phylogenetic Positions of Photsynthetic Bacteria Obtained from 5S RNA and 16S rRNA Sequence Data," *The Global Sulfur Cycle—NASA Technical Memorandum 87570* pp. 30–39 (1985).

Fox et al., "Classification of methanogenic bacteria by 16S ribosomal RNA characterization," *Proc. Natl. Acad. Sci. USA* 74:4537–4541 (1977).

Fox et al., "Comparative Cataloging of 16S Ribosomal Ribonucleic Acid Molecular Approach to Procaryotic Systematics," *International Journal of Systematic Bacteriology* 27:44–57 (1977).

Fox et al., "The phylogeny of prokaryotes," *Science* 209:457–463 (1980).

Fox and Woese, "5S rRNA secondary structure," *Nature* 256:505–507 (1975).

Fox and Woese, "The Architecture of 5S rRNA and Its Relation to Function", *J. Mo. Evol.* 6:61–76 (1975).

Freifelder, "Molecular Biology: A Comprehensive Introduction to Prokaryotes and Eukaryotes" Jones and Barlett Publishers, Inc., Boston (1983).

Galau et al., "Studies on Nucleic Acid Reassociation Kinetics: Retarded Rate of Hybridization of RNA with Excess DNA," *Proc. Natl. Acad. Sci. USA* 74:2306–2310 (1977).

Galpin et al., "The Use of Ribosomal DNA (rDNA) Hybridization for Detection of *Mycoplasma Pulmonis* in Chronically Infected Mouse Joints," *Official Abstract* vol. 47, No. 3 (1981).

Galpin et al., "The Use of Ribosomal DNA (rDNA) Hybridization for Detection of *Mycoplasma Pulmonis* in Chronically Infected Mouse Joints," Paper for 21st Interscience Conference on Antimicrobial Agents and Chemotherapy, Nov. 4–6 (1981).

Garvie and Farrow, "Sub–Divisions within the Genus Streptococcus Using Deoxyribonucleic Acid/Ribosomal Ribonucleic Acid Hybridizatoin," *Zbl. Bakt. Hyb., I. Abt. Orig.,* 2:299–310 (1981).

Gelb et al., "Quantitation of Simian Virus 40 Sequences in African Green Monkey, Mouse and Virus Transformed Cell Genomes," *J. Mol. Biol.* 57:129–145 (1971).

Gerbie et al., "Conserved Regions within Ribosomal DNA: Locations and Some Possible Functions," *The Cell Nucleus* 10:351–386 (1982).

Gibson et al., "A Phylogenetic Analysis of the Purple Photosynthetic Bacteria," *Current Microbiology* 3:59–64 (1979).

Gillis and De Ley, "Intra–and Intergeneric Similarities of the Ribosomal Ribonucleic Acid Cistrons of Acetobacter and Gluconobacter," *Intl. J. Syst. Bacteriol.* 30:7–27 (1980).

Giri et al., "Physical Characteristics of Protein–Deficient Particles Derived from the 50S Ribosomal Subunit," *Biochemistry* 15:5188–5192 (1976).

Glaser et al., "Physical Mapping of the Ribosomal RNA Genes of *Mycoplasma capricolum*," *Nucleic Acids Research* 12:2421–2427 (1984).

Göbel and Stanbridge, "Cloned Mycoplasm Ribosomal RNA Genes for the Detection of Mycoplasma Contamination in Tissue Cultures," *Science* 226:1211–1213 (1984).

Göbel et al., "Comparative Analysis of Mycoplasma Ribosomal RNA Opersons," *Israel J. Med. Sci.* 20:762–764 (1984).

Gobel et al., "Use of Cloned Mycoplasma Ribosomal Genes for Detection of Mycoplasma Contamination in Tissue Cultures," *Abstracts of the Annual Meeting of the American Society for Microbiology,* 84th Annual Meeting, St. Louis, Missouri, Mar. 4–9, 1984.

Gourse, "Location and possible roles of evolutionarily conserved regions within ribosomal RNA," *Diss. Abs. Int.* 41:4350–4351 (1981).

Gourse and Gerbi, "Fine Structure of Ribosomal RNA. III. Location of Evolutionarily Conserved Regions within Ribosomal DNA," *Journal of Molecular Biology* 140:321–339 (1980).

Gray et al., "On the evolutionary descent of organisms and organelles: a global phylogeney based on a highly conserved structural core in small subunit ribosomal RNA," *Nucleic Acids Research* 12:5837–5852 (1984).

Gutell and Fox, "A compilation of large subunit RNA sequences presented in a structural format," *Nucleic Acids Research* 16:r175–r183.

Gutell et al., "Comparative Anatomy of 16–S–like Ribosomal RNA," *Progress in Nucleic Acid Research and Molecular Biology* 32:155–216 (1985).

Hagenbuchle et al., "Conservation of the Primary Structure at the 3' End of 18S rRNA from Eucaryotic Cells," *Cell* 13:551–563 (1978).

Hill, "Application for a Laser, Digital Autocorrelator and Table for Quasi–elastic Light Scattering," *National Science Foundation Grant,* Nov. 30, 1982 –Apr. 30, 1984.

Hill, "Ribosomal Proteins: Synthesis and Structure," *Chemistry and Biochemistry of Amino Acids, Peptides and Proteins,* ed. B. Weinstein (Marcel Dekker:NY, 1981) vol. 6, pp. 1–31.

Hill, "Utilization of Ribosome Antigen in the Detection of Disease States".

Hill et al., "Effects of Solvent Environment and Mode of Preparation on the Physical Properties of Ribosomes from *Escherichia coli,*" *J. Mol. Biol.* 53:107–121 (1970).

Hill et al., "On the Sedimentation Behavior and Molecular Weight of 16S Ribosomal RNA from *Escherichia coli,*" *Nucleic Acids Research* 4:473–477 (1977).

Hill and Fessenden, "Structural Studies on the 30S Ribosome Subunit from *Escherichia coli,*" *J. Mol. Biol.* 90:719–726 (1974).

Holland et al., "Analysis of Virus Replication in Ageing Human Fibroblast Cultures," *Nature* 245:316–319 (1973).

Holland et al., "Defective Interfering Virus Particles Attenuate Virus Lethality In Vivo and In Vitro," in *Animal Virology*, ed. D. Baltimore, A.S. Huang, and C.F. Fox, (Academic Press Inc.:NY 1976) vol. IV, pp. 773–787.

Holland et al., "Long–Term Persistent Vesicular Stomatitis Virus and Rabies Virus Infection of Cells In Vitro," *J. gen. Virol.* 33:193–211 (1976).

Hogan et al., "Retinal Degeneration in Experimental Creutzfeldt–Jakob Disease," *Lab. Invest.* 49:708–715 (1983).

Hori and Osawa, "Evolutionary change in 5S RNA secondary structure and a phylogenic tree of 54 5S RNA species," *Proc. Natl. Acad. Sci. USA* 76:381–385 (1979).

Irbe and Oishi, "Prophage Injunction in a Permeabilized Cell System: Induction by DNases and the Role of recB-C–DNase," Abstract of the Annual Meeting of the American Society for Microbiology (1981), Publ. Health Res. Inst. of the City of New York.

Jacoli, "Attemps to Culture in vitro Mycoplasma–like Organisms from Plants: A Retrospective View, Phytopath 2" Laboratory of Biochemical Virology, Research Station, Agriculture Canada, Vancouver, B.C., Canada (1981) 102:148–152.

Jakovcic et al., "Sequence Homology Between Mitochondrial DNAs of Different Eukaryotes," *Biochemistry* 14:2043–2050 (1975).

Jakovcic et al., "Sequence Homology of Mitochondrial Leucyl–tRNA Cistron in Different Organisms," *Biochemistry* 14:2037–2042 (1975).

Jayaraman et al., "Selective inhibition of *Escherichia coli* protein synthesis and growth by nonionic oligonucleotides complementary to the 3' end of 16S rRNA," *Proc. Natl. Acad. Sci. USA* 78:1537–1541 (1981).

Johnson and Francis, "Taxonomy of the Clostridia: Ribosomal Ribonucleic Acid Homologies Among the Species," *J. Gen. Microbiol.* 88:229–244 (1975).

Johnson and Horowitz, "Characterization of Ribosomes and RNAs from *Mycoplasma hominis*," *Biochemica et Biophys. Acta* 247:262–279 (1971).

Kafatos et al., "Determination of nucleid acid sequence homologies and rleative concentrations by a dot hybridization procedure," *Nucleic Acids Research* 7:1541–1552 (1979).

Kan et al., "Prenatal Diagnosis of α–Thalassemia. Clinical Application of Molecular Hybridization," *New England Journal of Medicine* 295:1165–1167 (1976).

Kennell, "Principles and practices of nucleic acid hybridization," *Progr. Nucl. Acid Res. Mol. Biol.* 11:259–301 (1971).

Kettmann et al., "Leukemogensis by bovine leukemia virus: Proviral DNA integration and lack of RNA expression of viral long terminal repeat and 3' proximate cellular sequences," *Proc. Natl. Acad. Sci. USA* 79:2465–2469 (1982).

Khorana et al., "Polynucleotide Synthesis and the Genetic Code," (Cold Spring Harbor Symp.), *Quant Biol* 23:39–49 (1966).

Khorana, "Total Synthesis of a Gene," *Science* 203:614–625 (1979).

Kingsbury, Annual Progress Report, KROC Foundation Grant 1977–1978.

Kingsbury, "Evidence for an Unconvential Virus in Mouse-–Adapted Creutzfeldt–Jakob Disease", *Infection and Immunity* 37:1050–1053 (1982).

Kingsbury, "Evidence for Normal Cell–Mediated Immunity in Scrapie Infected Mice," *Infection and Immunity* 32:1176–1180 (1981).

Kingsbury, "Genetic Control of Scrapie and Creutzfeldt–Jakob Disease in Mice," *The Journal of Immunology* 131:491–496 (1983).

Kingsbury, "Molecular Probes for the Detection of Mycoplasma and Chlamydia in Rheumatoid Arthritis," Grant Application, May 11, 1977.

Kingsbury, "Rapid Detection of Mycoplasmas with DNA Probes," *Rapid Detections and Identification of Infectious Agents* pp. 219–233, Academic Press, Inc. (1985).

Kingsbury and Galpin, "Method of Detecting Mycoplasmataceae, Acholeplasmataceae and Spiroplasmataceae and Reagents Useful in Same," U.S. Patent Application.

Kissil, "Isolation and purification of ribosomal RNAs of *Euglena gracilis*: their evolutionary significance as determined by oligonucleotide catalogue analysis," *Diss. Abs. Int.* 42:471 (1981).

Klausner and Wilson, "Gene Detection Technology Opens Doors for Many Industries," *Biotechnology* pp. 472–478 (Aug. 1983).

Kohne Grant Proposal No. 16311–0 for period Sep. 1, 1979 to Aug. 31, 1981.

Kohne, "DNA Evolution Data and Its Relevance to Mammalian Phylogeny," *Proceedings of a Wenner–Gren Conference on the Phylogeny of Primates*, eds. Lucket and Szalay (Plenum Press:NY, 1975) p. 249.

Kohne, "Evolution of higher–organism DNA," *Quarterly Reviews of Biophysics* 3:327–375 (1970).

Kohne, "Isolation and Characterization of Bacterial Ribosomal RNA Cistrons," *Biophysical Journal* 8:1104–1118 (1968).

Kohne, "Ribosomal Ribonucleic Acid Synthesis in *Rana pipiens* Embryos," in *The Molecular Aspects of Biological Development*, N.A.S.A. Contractor Report CR–673, pp. 35 (1966).

Kohne, "Taxonomic Applications of DNA Hybridization Techniques", in *Chemotaxonomy and Serotaxonomy*, ed. J.G. Hawkes (Academic Press:NY, 1968) vol. 2, pp. 117–130.

Kohne, "The Isolation of Ribosomes from Eggs and Embryos of *Rana pipiens,*" *Ex. Cell Research* 38:211–213 (1964).

Kohne et al. "Evolution of Mammalian DNA," *Proceedings of the Sixth Berkeley Symposium on Mathematical Statistics and Probability* 5:193–209 (1972).

Kohne et al., "Evolution of Primate DNA Sequences," *J. Human Evolution* 1:627–644 (1972).

Kohne et al., "Room Temperature Method for Increasing the Rate of DNA Reassociation by Many Thousandfold: The Phenol Emulsion Reassociation Technique," *Biochemistry* 16:5329–5341 (1977).

Kohne et al., "Virus Detection by Nucleic Acid Hybridization: Examination of Normal and ALS Tissues for the Presence of Poliovirus," *J. Gen. Virol.* 56:223–233 (1981).

Kohne and Britten, "Hydroxyapatite Techniques for Nucleic Acid Reassociation," in *Procedures in Nucleic Acids Research*, eds. Cantoni and Davies, (Harper & Row:NY) vol. 2, pp. 500–512 (1972).

Kohne and Byers, "Amplification and Evolution of Dexoyribonucleic Acid Sequences Expressed as Ribonucleic Acid," *Biochemistry* 12:2373–2378 (1973).

Lampell and Riley "Evolutionary Events in *Escherichia coli* and *Salmonella typhimurium* Genomes," Abstract of the Annual Meeting of the American Society for Microbiology (1981), State University of New York. Stony Brook, New York.

Lane et al., "Rapid determiniation of 16S ribosomal RNA sequences for phylogenetic analysis," *Proc. Natl. Acad. Sci. USA* 82:6955–6959 (1985).

Langer et al., "Enzymatic Synthesis of biotin–labeled polynucleotides: novel nucleic acid affinity probes," *Proc. Natl. Acad. Sci. USA* 78:6633–6637 (1981).

LaRue et al., "The Evolution of Multi–isoacceptor tRNA Families," *J. Biol. Chem.* 256:1539–1543 (1981).

Lewin, "Synthesis and Assembly of Ribosomal Subunit," in *Gene Expression, Bacterial Genomes*, vol. 1, ed. B. Lewin (J. Wiley & Sons Ltd.:NY, 1974) vol. 1, pp. 122–131.

Lewin, "Transcription and Processing of RNA," *Gene Expression—Eucaryotic Chromosoms*, vol. 2, ed. B. Lewin (J. Wiley & Sons Ltd.:NY, 1974), ch. 5, pp. 229–319.

Link and Reiner, "A Novel Pattern of Catabolic Gene Arrangement in *E.coli*," Abstract of the Annual Meeting of the American Society for Microbiology (1980), University of Massachusetts, Amherst.

Lizardi and Engelberg, "Rapid Isolation of RNA Using Proteinase K and Sodium Perchlorate," *Analytical Biochemistry* 98:116–122 (1979).

Long and Dawid, "Expression of Ribosomal DNA Insertions in *Drosophila melanogaster*," *Cell* 18:1185–1196 (1979).

Lorian, "Antibiotics in Laboratory Medicine," V. Lorian ed. (Williams & Wilkens Company:Baltimore, 1980).

Luehrsen and Fox, "Secondary structure of eukaryotic cytoplasmic 5S ribosomal RNA," *Proc. Natl. Acad. Sci. USA* 78:2150–2154 (1981).

Mahler, "The Exon: Intron Structure of Some Mitochondrial Genes and Its Relation to Mitochondrial Evolution," *International Review of Cytology* 82:1–98 (1983).

Malcolm et al., "A comparison in situ hybridization techniques for gene localization," *Cytogenet. Cell Genet.* 19:256–261 (1977).

Mandel, "New Approaches to Bacterial Taxonomy: Perspective and Prospects," *Ann. Rev. Microbiology* 23:239–274 (1969).

Maniatis et al., *"Molecular Cloning—A Laboratory Manual,"* (Cold Spring Harbor Laboratory, 1982).

Mankin et al., "An enzymatic approach for localization of oligodeoxyribonucleotide binding sites on RNA," *FEBS Letters* 131:253–256 (1981).

Manning et al., "A Method of Gene Enrichment Based on the Avidin–Biotin Interaction. Application to the Drosophila Ribosomal RNA Genes," *Biochemistry* 16:1364–1370 (1977).

Maxwell et al., "Assay of DNA–RNA hybrids by $S_1$ nuclease digestion and adsorption to DEAE–cellulose filters", *Nucleic Acids Research* 5:2033–2038 (1978).

McCarthy and Church, "The Specificity of Molecular Hybridization Reactions," *Ann. Rev. Biochem.* 39:131–150 (1970).

Meinke et al., "Physical Properties of Cytoplasmic Membrane–associated DNA," *J. Mol. Biol.* 78:43–56 (1973).

Meinkoth and Wahl, "Hybridization of Nucleic Acids Immobilized on Solid Supports," *Analytical Biochemistry* 138:267–284 (1984).

Mills et al., "Purification and Partial Characterization of the Principal Deoxyribonucleic Acid Polymerase from Mycoplasmatales," *Journal of Bacteriology* 132:641–649 (1977).

Mochizuki et al., "Comparative Mitogenic Effects of Herpes Simplex Virus and Mycoplasma on Murine Lymphocytes," *J. Gen. Virol.* 54:185–190 (1981).

Moore et al., "Integration Transcription of Virus DNA in Herpes Simplex Virus Transformed Cell Lines," *J. Gen. Virol.* 48:123–133 (1980).

Moore, "Ribosomal ribonucleic acid cistron homologies among Hyphomicrobium and various other bacteria," *Can. J. Microbiol.* 23:478–481 (1977).

Moore and McCarthy, "Related Based Sequences in the DNA of Simple and Complex Organisms. III. Variability in the Base Sequence of the Reduplicated Genes for Ribosomal RNA in the Rabbit," *Biochemical Genetics* 2:75–86 (1968).

Moore and McCarthy, "Comparative study of Ribosomal Ribonucleic Acid Cistrons in Enterobacteria and Myxobacteria," *Journal of Bacteriology* 94:1066–1074 (1967).

Mordarski et al., "Ribosomal Ribonucleic Acid Similarities in the Classification of Rhodococcus and Related Taxa," *Journal of General Microbiology* 118:313–319 (1980).

Morgan and Kaplan, "Transcription of *Escherichia coli* Ribosomal DNA in *Proteus mirabilis*," *Molec. Gen. Genet.* 147:179–188 (1976).

Mosely et al., "Identification of Enterotoxigenic *E. coli* by Colony Hybridization Using Three Enterotoxin Gene Probes," *J. of Infect. Diseases* 145:863–869 (1982).

Moss and Bryant, "DNA:rRNA Hybridization Studies of *Chromobacterium fluviatile*," *J. Gen. Microbiol.* 128:829–834 (1982).

Mottice and Wilson, "Analysis of Integration in *Bacillus subtilis* with Recombinant Plasmids," Abstract of the Annual Meeting of the American Society for Microbiology (1981), University of Rochester Medical Center, Rochester, New York.

Neimark, "Evolution of Mycoplasmas and Genome Losses," *The Yale Journal of Biology and Medicine* 56:377–383 (1983).

Nickoloff and Hallick, "Synthetic deoxyoligonucleotides as general probes for chloroplast transfer RNA genes," *Nucleic Acids Research* 10:8191–8210 (1982).

Nicholson et al., "Studies on Extreme Halophile 5S rRNAs," (FILL IN).

Nisen and Shapiro, "*E coli* Ribosomal RNA Contains Sequences Homologous to Insertion Sequences 1S1 and 1S2," *Nature* 282:872–874 (1979).

Noller, "Structure of Ribosomal RNA," *Ann. Rev. Biochem.* 53:119–62 (1984).

Noyes et al., "Detection and partial sequence analysis of gastrin mRNA by using an oligodeoxynucleotide probe," *Proc. Natl. Acad. Sci. USA* 76:1770–1774 (1979).

Olins et al., "Conformational States of Chromatin v. Bodies Induced by Urea," *Nucleic Acids Research* 4:1911–1933 (1977).

Olmedilla et al., "Variability in Giant Fennel (*Ferula communis*, Umbelliferae): Ribosomal RNA Nuclear Genes," *Plant Systems and Evolution* 150:263–274 (1985).

Oostra et al., "A Rapid and Sensitive Determination of Bacterial rRNA by Means of Hybridizatoin–Competition," *Analytical Biochemistry* 74:496–502 (1976).

Ortega and Hill, "A Molecular Weight Determiniation of the 16S Ribosomal Ribonucleic Acid from *Escherichia coli*," *Biochemistry* 12:3241–3243 (1973).

Pace and Campbell, "Homology of Ribosomal Ribonucleic Acid of Diverse Species with *Escherichia coli* and *Bacillus stearothermophilus*," *Journal of Bacteriology* 107:543–547 (1971).

Patterson and Stafford, "Sea Urchin Satellite Deoxyribonucleic Acid. Its Large–Scal Isolation and Hybridization with Homologous Ribosomal Ribonucleic Acid," *Biochemistry* 9:1278–1282 (1970).

Pechman and Woese, "Characterization of the Primary Structural Homology Between the 16S Ribosomal RNAs of *Escherichia coli* and *Bacillus megaterium* by Oligomer Cataloging," *J. Mol. Evol.* 1:230–240 (1972).

Pedersen and Kjeldgaard, "A Hybridization Assay Specific for Ribosomal RNA from *Escherichia coli*," *Molec. Gen. Genet.* 118:85–91 (1972).

Pollack and Williams, "Identification of an Inorganic Pyrophosphate Dependent Phosphofructokinase from Acholeplasma laidlwaii B–PG9," *Abstracts of the Annual Meeting of the American Society for Microbiology* G20 (1984).

Portnoy et al., "Genetic Analysis of Essential Plasmid Determinants of Pathogenicitiy in *Yersinia pestis*" *Journal of Infectious Diseases* 148:297–304 (1983).

Pressley et al., "Gene deletions in α thalassemia prove that the 5'ζ locus is functional," *Proc. Natl. Acad. Sci. USA* 77:3586–3589 (1980).

Pribula et al., "Nucleotide Sequence of *Bacillus Megaterium* 5 S RNA," *FEBS Letters* 44:322–323 (1974).

*Principles in Biochemistry*, 7th ed., Smith et al. eds., McGraw-Hill, New York, NY p. 795 (1983).

Puga et al., "Homology Between the Genomes of Bacteriophage S13 and *Escherichia coli*," *Virology* 43:507–510 (1971).

Razin et al., "Characterization of the Mycoplasma Genome," *The Yale Journal of Biology and Medicine* 56:357–366 (1983).

Razin et al., "Detection of mycoplasmas infecting cell cultures by DNA Hybridization," *In Vitro* 20:404–408 (1984).

Razin et al., "Molecular and Biological Features of Mollicutes (Mycoplasmas)," *Ann. Microbiol.* 135:9–15 (1984).

Razin et al., "Mycoplasmal Ribosomal RNA Genes and Their Use As Probes for Detection and Identification of Mollicutes," *Israel Journal of Medical Sciences* 20:758–761 (1984).

Reff et al., "Phylogenetic Relationships Between Mycoplasma and Other Procaryotes Based Upon the Electrophoretic Behavior of Their Ribosomal Ribonucleic Acids," *Intl. J. Syst. Bacteriol.* 27:185–193 (1977).

Reff, "Phylogenetic Relationships of Prokaryotes Based on Characterization of Their Ribosomal RNA," Microbiology, Dissertation Abstracts International, Apr. 1977, vol. 37, No. 10 pp. 4893–4894.

Reff, "Phylogenetic Relationships of Prokaryotes Based on Characterization of Their Ribosomal RNA," Dissertation to the Department of Medical Microbiology and the Committee on Graduate Studies of Stanford University (Aug. 1976).

Reff and Stanbridge, "Conformational Differences in Bacterial Ribosomal RNAs in Non–Denaturing Conditions," *Nature* 260:724–726 (1976).

Reich et al., "Genetic Differentiation by Nucleic Acid Homology," *Journal of Bacteriology* 92:302–310 (1966).

Reich et al., "Genetic Relatedness Among Mucoplasmas as Determined by Nucleic Acid Homology," *Journal of Bacteriology* 91:153–160 (1966).

Reichmann et al., "RNA Polymerase Activity and Poly(A) Synthesizing Activity in Defective T Particles of Vesicular Stomatitis Virus," *Virology* 58:240–249 (1974).

Ryan and Morowitz, "Partial Purification of Native rRNA and tRNA Cistrons from Mycoplasma SP.(KID)," *Biochemistry* 63:12882–1289 (1969).

Sanger et al., "DNA sequencing with chain–terminating inhibitors," *Proc. Natl. Acad. Sci. USA* 74:5463–5647 (1977).

Sawada et al., "The Number of Ribosomal RNA Genes in *Mycoplasma capricolum*," *Molec. Gen. Genet.* 182:502–504 (1981).

Schneider and Stanbridge, "Comparison of Methods for the Detection of Mycoplasmal Contamination of Cell Cultures: A Review," *In Vitro* 11:20–34 (1975).

Schneider and Stanbridge, "Mycoplasma Contamination of Cultured Amniotic Fluid Cells: Potential Hazard to Prenatal Chromosomal Diagnosis," *Science* 184:477–480 (1974).

Schneider et al., "Incorporation of H–Uridine and H–Uracil Into RNA (A Simple Technique for the Detection of Mycoplasma Contamination of Cultured Cells)," *Experimental Cell Research* 84:311–318 (1974).

Schomer et al., "The Application of Digital Image Processing for the Automation of 16SrRNA Oligonucleotide Fingerprint Analysis (Abstract)," *Conference on Automation of Diagnostic Cytology: Abstracts*, Sep. 1983, vol. 5, No. 3, p. 219.

Scolnick et al., "Primate and Murine Type–C Viral Nucleic Acid Association Kinetics: Analysis of Model Systems and Natural Tissues," *Journal of Virology* 13:363–369 (1974).

Seet et al., "Binding of Tetranucleotides to the 5 S RNA from the Rat Liver," *Molecular Biology* 8:575–579 (1974).

Selker, "Structure, expression and evolution of 5S RNA, 5.8S rRNA and tRNA$^{Phe}$ genes from *Neurospora crassa* and TRP genes from *Salmonella typhimurium*," *Dissertation Abstracts International* 41:4007 (1981).

Setterquist et al., "Characterization of the msp–113 Gene Cluster in Strains of *Caenorhabditis elegans*," Dept. of Biochemical Sciences, University of Houston, Houston, Texas.

Setterquist et al., "Progress in the Characterization of the msp Gene Family in *Caenorhabditis vulgariensis*," Dept. of Biochemical Sciences, University of Houston, Houston, Texas.

Sgaramella et al., "Isolation of the Hybrid Between Ribsomal RNA and DNA of *Bacillus subtilis*," Cold Spring Harbor Symp. Quant. Biol., 1968, vol. 33, pp. 839–842.

Shih et al., "A General Method of Gene Isolation," *Proc. Natl. Acad. Sci. USA* 70:1697–1700 (1973).

Shih and Martin, "General method of gene isolation," *Biochem. Methods* 79:143 (1973).

Sinclair et al., "Retention of Common Nucleotide Sequences in the Ribosomal Dexoynucleic Acid of Eukaryotes and Some of Their Physical Characteristics," *Biochemistry* 10:2761–2769 (1971).

Sobieski et al., "rRNA oligonucleotide catalog data base," *Nucleic Acids Research* 12:141–148 (1984).

Sogin et al., "Phylogenic Measurement in Procaryotes by Primary Structural Characterization," *J. Mol. Evol.* 1:173–184 (1972).

Sollner–Webb and McKnight, "Accurate Transcription of Cloned Xenopus rRNA Genes by RNA Poymerase I: Demonstration by S1 Nuclease Mapping," *Nucleic Acids Research* 11:3391–3405 (1982).

Sollner–Webb and Reeder, "The Nucleotide Sequence of the Initiation and Termination Sites for Ribosomal RNA Transcription in *X. laevis*," *Cell* 18:485–499 (1979).

Somerson et al., "Genetic Differentiation by Nucleic Acid Homology," *Journal of Bacteriology* 92:311–317 (1966).

Soot et al., "Binding of Tetranucleotides with 5S RNA from Rat Liver," (Russian Document) 1974 –7234–728.

Stackebrandt and Woese, "A Phylogenetic Dissection of the Family Micrococcaceae," *Current Microbiology* 2:317–322 (1979).

Stackebrandt et al., "The Phylogenetic Structure of the Coryneform Group of Bacteria," *Zbl. Bakmt. Hygg., I. Abt. Orig.* C1:137–149 (1980).

Staley and Krieg, "Classification of Procaryotic Organisms: An Overview," *Bergey's Manual of Systematic Bacteriology,* ed. Noel R. Krieg (Williams & Wilkins:Baltimore 1971) vol. 1, pp. 1–4.

Stanbridge, "A Reevaluation of the Role of Mycoplasmas in Human Disease," *Ann. Rev. Microbiology* 30:169–187 (1976).

Stanbridge, "Infectious Diseases in the Twilight Zone (Mycoplasma, Chyamydia, Rickettsia et al.)," The University of Sydney, The Post–Graduate committee in Veterinary Science, Proc. No. 27 (Feb. 1976).

Stanbridge, "Molecular Probes to Detect Fastidious Mycoplasma Pathogens," Molecular Probes to Detect Mycoplasma Pathogens, Grant Application, Jul. 1, 1976.

Stanbridge, "Mycoplasmas and Cell Cultures," *Bacteriological Reviews* 35:206–227 (1971).

Stanbridge, "Mycoplasma Detection—An Obligation to Scientific Accuracy," *Israel J. Med. Sci.* 17:563–568 (1981).

Stanbridge, "Mycoplasma–Lymphocyte Interactions and Their Possible Role in Immunopathologic Manifestations of Mycoplasmal Disease," *Reviews of Infectious Diseases* 4:S219–S226 (1982).

Stranbridge and Gobel, "Mycoplasma Detection in Cultured Cell Lines. A Reply," *Microbiology and Molecular Genetics UC, Irvine, Ludwig University, West Germany.*

Standbridge and Katayama, "Indirect Detection Methods for Mycoplasma Contaminants of Cell Cultures," *Morphological and Biochemical Methods for Detection* pp. 72–86.

Stanbridge and Reff, "The Molecular Biology of Mycoplasmas," *The Mycoplasmas* 1:157–185 (1979).

Stanbridge and Schneider, "The Need for Non–Cultural Methods for the Detection of Mycoplasma Contaminants," *Develop. Biol. Standard.* 37:191–200 (1977).

Stehelin et al., "Purification of DNA Complementary to Nucleotide Sequences Required for Neoplastic Transformation of Fibroblasts by Avian Sarcoma Viruses," *J. Mol. Biol.* 101:349–365 (1976).

Stewart et al., "Characterization of Cloned Ribosomal RNA Sequences from *Bacillus subtilis*," Abstract of the Annual Meeting of the American Society for Microbiology (1981), University of North Carolina, Chapel Hill.

Stiegler et al., "A General Secondary–Structure Model for Procaryotic and Eucaryotic RNAs of the Small Ribosomal Subunits," *Eur. J. Biochem.* 120:484–492 (1981).

Suggs et al., "Use of synthetic oligonucleotides as hybridization probes: Isolation of cloned cDNA sequences for human $\beta_2$–microglobulin," *Proc. Natl. Acad. Sci. USA* 78:6613–6617 (1981).

Sugino et al., "Partial Nucleotide Sequence Similarity within Species Mycoplasma and Acholeplasma," *J. Gen Micro.* 121:333–338 (1980).

Summers and Hume, "Mycoplasma Detection in Cultured Cell Lines," Department of Human Biology and Department of Medicine and Clinical Science, John Curtin School of Medical Research, Australian National University.

Swings et al., "Frateuria, a New Genus for *Acetobacter aurantius*," *International Journal of Systematic Bacteriology* 30:547–556 (1980).

Szabo et al., "Quantiative in Situ Hybridization of Ribosomal RNA Species to Polytene Chromosomes of *Drosophila melanogaster*," *J. Mol. Biol.* 115:539–563 (1977).

Takahashi, "An Attempt to Concentrate Ribosomal RNA Cistrons in *Bacillus subtilis* by Millipore Filtration," *Biochemica et Biophys. Acta* 190:124–216 (1969).

Takahashi and Saito, "Genetic Relatedness in Several Species of Bacteria Studies by the DNA–DNA and DNA–Ribosomal RNA Hybridization Methods," *Culture Collections of Microorganisms*, Proceedings of the International Conference on Culture Collections — Tokyo (Oct. 7–11, 1968) pp. 411–421 (1970).

Takahashi and Saito, "Species Specificity of the Ribosomal RNA Cistrons in Bacteria," *Biochemica et Biophys. Acta* 134:124–133 (1967).

Tam and Hill, "Physical Characteristics of the Reconstitution Intermediates ($RI_{30}$ and $RI_{*30}$) from the 30S Ribosomal Subunit of *Escherichia coli*," *Biochemistry* 20:6480–6484 (1981).

Tam and Hill, "Physical Characteristics of the Activated Reconstitution Intermediate (R1*) from the 30S Ribosomal Subunit of *Escherichia coli*," *Biochemistry International* 3:655–662 (1981).

Tam and Hill, "Physical Characteristics of the Reconstitution Intermediates $RI_{50(1)}$ from the 50S Ribosomal Subunit of *Escherichia coli*," *FEBS Letters* 120 (Nov. 1980).

Tam et al., "Physical Characteristics of the 16S rRNA Under Reconstitution Conditions," *J. Biol. Chem.* 256:6430–6434 (1981).

Tam et al., "Physical Characteristics of 23S rRNA from the 50S Ribosomal Subunit of *E. coli*," *FEBS Letters* 130:217–220 (1981).

Taniguchi and Weissmann, "Inhibition of Q$\beta$ RNA 70S ribosome initiation complex formation by an oligonucleotide complementary to the 3' terminal region of *E. coli* 16S ribosomal RNA," *Nature* 275:770–772 (1978).

Tapprich and Hill, "Involvement of Bases 787–795 of *Escherichia coli* 16S Ribosomal RNA in Ribosomal Subunit Association," *Proc. Natl. Acad. Sci. USA* 83:556–560 (1986).

Taylor et al., "Efficient Transcription of RNA into DNA by Avian Sarcoma Virus Polymerase," *Biochemica et Biophys. Acta* 442:324–330 (1976).

Taylor et al., "Induction of Species–Crossreactive Antibodies by Products Expressed from Cloned Genomic Sequences of *Mycoplasma hyorhinis*," Abstracts of the General Meeting of the American Society for Microbiology (1984) 86:G21.

Taylor et al., "Use of Specific Radioactive Probes to Study Transcription and Replication of the Influenze Virus Genome," *Journal of Virology* 21:530–540 (1977).

Thomas, "Hybridization of Denatured RNA and Small DNA Fragments Transferred to 86 Nitrocellulose," *Proc. Natl. Acad. Sci. USA* 77:5201–5205 (1980).

Timberlake, "Development Gene Regulation in *Aspergillus nidulans*" *Developmental Biology* 78:497–510 (1980).

Treco et al., "The Ribosomal Gene Nontranscribed Spacer," *The Cell Nucleus* 12:101–126 (1982).

Truper and Krämer, "Principles of Characterization and Identification of Prokaryotes," in *The Prokaryotes. A Handbook on Habitats, Isolation, and Identification of Bacteria*, eds. Starr, Stolp, Trüper, Balows and Schlegel (Springer–Verlag:Berlin (1981) vol. 1, pp. 176–193.

Tu et al., "Taxonomic Relations Between Archaebacteria Including 6 Novel Genera Examined by Cross Hybridization of DNAs and 16S rRNAs," *J. Mol. Evol.* 18:109–114 (1982).

Van Holde and Hill, "General Physical Properties of Ribosomes," *Ribosomes* pp. 53–91 (1974).

Wagner and Gassen, "On the covalent binding of mRNA models to the part of the 16 S RNA which is located in the mRNA binding site of the 30 S ribosome," *Biochem. and Biophys. Res. Comm.* 65:519–529 (1975).

Walker et al., "Conditions for the Chemical and Physical Inactivation of the K. Fu. Strain of Agent of Creutzfeldt––Jakob Disease," *Amer. Journal of Public Health* 73:661–665 (1983).

Wallace et al., "Hybridization of synthetic oligodeoxyribonucleotides to $\phi_x$ 174 DNA: the effect of single base pair mismatch," *Nucleic Acids Research* 6:3543–3557 (1979).

Ware et al., "Sequence analysis of 28S ribosomal DNA from the amphibian *Xenous laevis*," *Nucleic Acids Research* 11:7795–7817 (1983).

Weeks et al., "Two Site Immunochemiluminometric Assay for Human $\alpha_1$–Fetoprotein," *Clin. Chem.* 29:1480–1483 (1983).

Wetmur, Acceleration of DNA Renaturation Rates, *Biopolymers* 14:2517–2524 (1975).

Wetmur and Davidson, "Kinetics of Renaturation of DNA," *J. Mol. Biol.* 31:349–370 (1968).

Wilson et al., "Individual and Evolutionary Variation of Primate Ribosomal DNA Transcription Initiation Regions," *Mol. Biol. Evol.* 1:221–237 (1984).

Wirth and Pratt, "Rapid identification of Leishmania species by specific hybridization of kinetoplast DNA in cutaneous lesions," *Proc. Natl. Acad. Sci. USA* 76:6999–7003 (1982).

Wisotzkey et al., "16S rRNA Sequence Analysis Among the Thermophilic Bacillus Species Indicates that the Thermophilic Phenotype is a Valid Express of Phylogenetic History," *Abstract* University of Houston, Houston, Texas.

Woese, "Archaebacteria," *Scientific American*, 244:2–15 (1981) 98–102.

Woese et al., "Archaebacteria," *J. Mol. Evol.* 11:245–252 (1978).

Woese et al., "Conservation of primary structure in 16S ribosomal RNA," *Nature* 254:83–86 (1975).

Woese et al., "Phylogenetic analysis of the mycoplasmas," *Proc. Natl. Acad. Sci. USA* 77:494–498 (1980).

Woese et al., "Procaryote Phylogeny — I. Concerning the Relatedness of Aerobacter aerogenes to *Escherichia coli*," *J. Mol. Evol.* 3:293–299 (1974).

Woese et al., "The Nucleotide Sequence of the 5S Ribosomal RNA from a Photobacterium," *J. Mol. Evol.* 5:35–46 (1975).

Woese et al., "Secondary structure model for bacterial 16S ribosomal RNA: phylogenetic, enzymatic and chemical evidence," *Nucleic Acids Research* 8:2275–2293 (1980).

Woese et al., "Sequence Characterization of 5S Ribosomal RNA from Eight Gram Positive Procaryotes," *J. Mol. Evol.* 8:143–153 (1976).

Woese and Fox, "Methanogenic Bacteria," *Nature* 273:101 (1978).

Woese and Fox, "Phylogenetic Structure of the Prokaryotic Domain: The Primary Kingdoms," *Proc. Natl. Acad. Sci. USA* 74:5088–5090 (1977).

Woese and Fox, "The Concept of Cellular Evolution" *J. Mol. Evol.* 10:1–6 (1977).

Wrede et al., "Binding Oligonucleotides to *Escherichia coli* and *Bacillus stearothermophilus* 5S RNA," *J. Mol. Biol.* 120:83–96 (1978).

Youvan, "Reverse Transcriptase Pauses at $N^2$–methylguanine during in vitro transcription of *Escherichia coli* 16S ribosomal RNA," *Proc. Natl. Acad. Sci. USA* 8:3751–3754 (1979).

Yu et al., "Synthesis of Oligo–and Polynucleotides — XXI. The Chemical Synthesis of Two Dodecanucleotides Complementary to the 5'–Terminal Sequence of 16 S rRNA of *E. coli*," *Bioorgan. Khimiya* 5:1181–1900 (1979).

Zablen, "Procaryotic Phylogeny by Ribosomal Ribonucleic Acid Sequence Homology," Microbiology, Dissertation Abstracts International, Nov. 1976, vol. 37, No. 5 p. 2083.

Zablen et al., "Phylogenetic Origin of the Chloroplast and Prokaryotic Nature of Its Ribosomal RNA," *Proc. Natl. Acad. Sci. USA* 72:2418–2422 (1975).

Zimmermann et al., "Molecular Cloning and Selection of Genes Regulated in Aspergillus Development," *Cell* 21:709–715 (1980).

Ito et al. J. Gen. Virol (1979) 43:103–110.

Kitahara et al. (1976) Antimicrobial Agents & Chemotherapy 9(6):908–914.

Anhalt (1980) in Manual of Clinical Microbiology 3rd eds. Lennetle et al, eds; Society Micro. Wash. DC.

METHOD FOR DETERMINING THE SENSITIVITY OF MICROORGANISMS TO ANTI MICROBIAL AGENTS USING RIBOSOMAL NUCLEIC ACID HYBRIDIZATION

RELATED APPLICATIONS

This is a division of application Ser. No. 08/199,486, filed Feb. 22, 1994, which is a continuation of Kohne, U.S. Ser. No. 08/179,922, filed Jan. 11, 1994 now abandoned which is a continuation of Ser. No. 07/857,081, filed Mar. 19, 1992, now U.S. Pat. No. 5,288,611, which is a continuation of Ser. No. 07/584,432, filed Sep. 12, 1990, now abandoned, which is a continuation of Ser. No. 07/464,717, filed Jan. 12, 1990, now abandoned, which is a continuation of Ser. No. 07/353, 208, filed May 17, 1989, now abandoned, which is a continuation of Ser. No. 06/655,365, filed Sep. 4, 1984, now abandoned, which is a continuation-in-part of Ser. No. 06/456,729, filed Jan. 10, 1983, now abandoned, all entitled "Method for Detecting, Identifying and Quantitating Organisms and Viruses", all hereby incorporated by reference herein.

TECHNICAL FIELD

The invention relates to a method and means for detecting, identifying, and quantitating organisms in biological and other samples. Thus, it relates to a method for specifically and sensitively detecting and quantitating any organism containing the ribosomal RNA, (hereinafter R-RNA), transfer RNA (hereinafter t-RNA) or other RNA, any members or large, intermediate, or small sized categories or taxonomic groups of such organisms; and previously unknown organisms containing R-RNA or t-RNA. The method is capable of detecting the presence of even one organism, containing R-RNA or t-RNA.

The invention also involves a method for using specifically produced nucleic acids complementary to specific sequences or populations of different sequences of the RNA class mRNA, or hnRNA, or snRNA, or the class of RNA sequences (hereinafter precursor specific RNA sequences or bsRNA) which are present only in the precursor mRNA, R-RNA, t-RNA, hnRNA or snRNA molecules, and not in mature mRNA, R-RNA, t-RNA, hnRNA or snRNA molecules, to detect, identify, and quantitate specific organisms, groups of organisms, groups of eukaryotic cells or viruses in cells.

My invention and the novelty, utility, and unobviousness thereof can be more clearly understood and appreciated when considered in light of the representative background information hereinafter set out, comprising this art.

BACKGROUND ART

Each of the cells of all life forms, except viruses, contain ribosomes and therefore ribosomal RNA. A ribosome contains three separate single strand RNA molecules, namely, a large molecule, a medium sized molecule, and a small molecule. The two larger R-RNA molecules vary in size in different organisms.

Ribosomal RNA is a direct gene product and is coded for by the R-RNA gene. This DNA sequence is used as a template to synthesize R-RNA molecules. A separate gene exists for each of the ribosomal RNA subunits. Multiple R-RNA genes exist in most organisms, many higher organisms containing both nuclear and mitochondrial R-RNA genes. Plants and certain other forms contain nuclear, mitochondrial and chloroplast R-RNA genes. For simplicity of discussion hereinafter, the three separate R-RNA genes will be referred to as the R-RNA gene.

Numerous ribosomes are present in all cells of all life forms. About 85–90 percent of the total RNA in a typical cell is R-RNA. A bacteria such as $E.$ $coli$ contains about $10^4$ ribosomes per cell while a mammalian liver cell contains about $5 \times 10^6$ ribosomes. Since each ribosome contains one of each R-RNA subunit, the bacterial cell and mammalian cell contains $10^4$ and $5 \times 10^6$, respectively, of each R-RNA subunit.

Nucleic acid hybridization, a procedure well-known in the art, has been used in the prior art to specifically detect extremely small or large quantities of a particular nucleic acid sequence, even in the presence of a very large excess of non-related sequences. Prior art uses of nucleic acid hybridization are found, for example, in publications involving molecular genetics of cells and viruses, genetic expression of cells and viruses; genetic analysis of life forms; evolution and taxonomy or organisms and nucleic acid sequences; molecular mechanisms of disease processes; diagnostic methods for specific purposes, including the detection of viruses and bacteria in cells and organisms.

Probably the best characterized and most studied gene and gene product are the R-RNA gene and R-RNA, and the prior art includes use of hybridization of R-RNA and ribosomal genes in genetic analysis and evolution and taxonomic classification of organisms and ribosomal gene sequences. Genetic analysis includes, for example, the determination of the numbers of ribosomal RNA genes in various organisms; the determination of the similarity between the multiple ribosomal RNA genes which are present in cells; determination of the rate and extent of synthesis of R-RNA in cells and the factors which control them. Evolution and taxonomic studies involve comparing the R-RNA gene base sequence from related and widely different organisms.

It is known that the ribosomal RNA gene base sequence is at least partially similar in widely different organisms, and that the DNA of $E.$ $coli$ bacterial ribosomal RNA genes hybridizes well with R-RNA from plants, mammals, and a wide variety of other bacterial species. The fraction of the $E.$ $coli$ gene which hybridizes to these other species varies with the degree of relatedness of the organisms. Virtually all of the R-RNA gene sequence hybridizes to R-RNA from closely related bacterial species, while less hybridizes to R-RNA from distantly related bacterial species, and even less with mammalian R-RNA.

As with R-RNAs, t-RNAs are present in all living cells, as well as in some viruses. t-RNA genes are present in chromosomal and plasmid DNAs of prokaryotes and in the DNA of eukaryotic cells, including the DNA of the nucleus, mitochondria and chloroplasts. Different t-RNA genes for one t-RNA species often exist in a single cell. t-RNA genes of mitochondria, nucleic and chloroplasts are quite different. Many virus genomes include genes for t-RNAs which are specific to the virus.

t-RNA molecules are direct gene products and are synthesized in the cells using the t-RNA gene as a template. The t-RNA is often synthesized as part of a larger RNA molecule, and the t-RNA portion is then removed from this precursor molecule. After synthesis a fraction of the bases of the t-RNA molecule are chemically modified by the cell. A typical t-RNA molecule contains from 75–85 bases.

Numerous t-RNA molecules are present in all cells of all life forms, and usually about 10 percent of a cell's total RNA is composed of t-RNA, a typical bacterial cell containing about $1.5 \times 10^5$ t-RNA molecules of all types. If each different kind of t-RNA is equally represented in a bacterial cell then 2500 of each different t-RNA molecule is present in each cell. A typical mammalian liver cell contains about $10^8$ t-RNA molecules or an average of about $10^6$ copies per cell of each different t-RNA type.

During protein synthesis individual amino acids are aligned in the proper order by various specific t-RNAs, each amino acid being ordered by a different t-RNA species. Some amino acids are ordered by more than one t-RNA type.

There are certain viruses which contain t-RNA genes in their genomes, these genes producing virus specific t-RNA when the virus genome is active in a cell. These t-RNAs can also be present in multiple copies in each infected cell.

As with R-RNA genes and R-RNA, the prior art discloses use of hybridization of t-RNA and t-RNA genes in genetic analysis and evolution and taxonomic classification of organisms and t-RNA gene sequences. Genetic analysis includes, for example, the determination of the numbers of t-RNA genes in various organisms; the determination of the similarity between the multiple t-RNA genes which are present in cells; determination of the rate and extent of synthesis of t-RNA in cells and the factors which control them. Evolution and taxonomic studies involve comparing the t-RNA gene base sequence from related and widely different organisms.

And as with R-RNA gene base sequences, it is known that an individual t-RNA gene base sequence is at least partially similar in different organisms. Total t-RNA shows this same type of relationship and bulk t-RNA from one species will hybridize significantly with t-RNA genes of a distantly related organisms. Rat mitochondrial leucyl-t-RNA hybridized significantly with mitochondria DNA of chicken and yeast (Biochemistry (1975) 14, #10, p. 2037). t-RNA genes have also been shown to be highly conserved among the members of the bacterial family Enterobacteriaceae. Bulk t-RNA genes from *E. coli* hybridize well with t-RNA isolated from species representing different genes (J. Bacteriology (1977) 129, #3, p. 1435–1439). The fraction of the *E. coli* t-RNA/gene which hybridizes to these other species varies with the degree of relatedness of the organisms. A large fraction of the *E. coli* t-RNA gene sequence hybridizes to t-RNA from a closely related species while much less hybridized to R-RNA from distantly related species.

The extent of conservation of the t-RNA gene sequences during evolution is not as great as that for the R-RNA gene sequences. Nonetheless the t-RNA gene sequences are much more highly conserved than the vast bulk of the DNA sequences present in cells.

The sensitivity and ease of detection of members of specific groups of organisms by utilizing probes specific for the R-RNA or t-RNA of that group of organisms is greatly enhanced by the large number of both R-RNA and t-RNA molecules which are present in each cell. In addition the hybridization test is made significantly easier since RNA molecules present in cells are single stranded. Thus a denaturation step, such as must be used for a hybridization test which detects any fraction of cell DNA, is not necessary when the target molecule is RNA. Probes specific for other classes of cell nucleic acids, besides R-RNA or t-RNA, may be used to specifically detect, identify and quantitate specific groups of organisms or cells by nucleic acid hybridization. Thus, other classes of RNA in prokaryotic cells include messenger RNA (hereinafter mRNA), and RNA sequences which are part of a variety of precursor molecules. For example R-RNA is synthesized in the bacteria *E. coli* as a precursor molecule about 6000 bases long. This precursor molecule is then processed to yield the R-RNA subunits (totaling about 4500 bases) which are incorporated into ribosomes and the extra RNA sequences (1500 bases in total) which are discarded. t-RNA molecules and ribosomal 5S RNA are also synthesized and processed in such a manner.

In prokaryotic cells infected by viruses there is also virus specific mRNA present. The mRNAs of certain prokaryotic viruses are also synthesized as a precursor molecule which contains excess RNA sequences which are trimmed away and discarded.

Many of the prokaryotic mRNAs and virus mRNAs are present up to several hundred times per cell while thousands of the excess RNA sequences present in R-RNA or t-RNA precursor molecules can be present in each cell.

Eukaryotic cells also contain precursor mRNA, as well as precursor R-RNA and t-RNA, molecules which are larger than the final R-RNA or t-RNA molecules. In contrast to prokaryotes, many newly synthesized eukaryotic mRNA molecules are much larger than the final mRNA molecule and contain excess RNA sequences which are trimmed away and discarded. Another class of RNA present in eukaryotic cells is heterogeneous nuclear RNA (hereinafter known as hn-RNA), which is a diverse class of RNA which contains mRNA precursor molecules (which leave the nucleus for the cytoplasm where protein synthesis occurs) and a large amount of RNA which never leaves the nucleus. This fraction also contains a small fraction of double strand RNA. Eukaryotic nuclei also contain small RNA molecules called small nuclear RNA (hereinafter snRNA), varying in length from 100–200 bases.

The abundance, or number of copies per cell, of different mRNA molecules varies greatly. This varies from a complex class of mRNA molecules which are present only 1–2 times per cell, to the moderately abundant class of RNA molecules which are present several hundred times per cell, to the superabundant class of RNA molecules which may be present $10^4$ or more times per cell. Many of the RNA sequences present in hnRNA are also very abundant in each cell. The RNA sequences present in the precursor RNA molecules for R-RNA, t-RNAs and many mRNAs are also very abundant in each cell. Individual snRNA sequences are extremely abundant and may be present from $10^4$ to $10^6$ times per cell.

Eukaryotic cells are also infected by viruses which produce virus specific mRNA and in may cases virus specific precursor mRNA molecules which contain RNA sequences not present in the mature mRNA molecule. The individual virus specific mRNA and precursor RNA molecules vary in abundance from complex (1–2 copies per cell) to superabundant (around $10^4$ copies per cell).

My invention also relates therefore, to a method for specifically and sensitively detecting, identifying and quantitating organisms, as well as, viruses, present in cells. More particularly, the method is useful for sensitively detecting, identifying and quantitating any member of different sized categories of organisms, eukaryotic cells, viruses, and in some cases previously unknown organisms containing mRNA, hnRNA, snRNA or excess RNA molecules present in R-RNA, t-RNA, mRNA, or hnRNA molecules.

This invention therefore has broad application to any area in which it is important to determine: the presence or absence of living organisms, or viruses present in cells; the state of genetic expression of, an organism, cell, virus present in a cell, or groups of cells of prokaryotic or eukaroytic organisms. Such areas include medical, veterinary, and agricultural diagnostics and industrial and pharmaceutical quality control.

The invention involves a method for using specifically produced nucleic acids complementary to, not only R-RNA and t-RNA, but also to specific sequences or populations of different sequences of the RNA class mRNA or hnRNA as snRNA or the class of RNA sequences (hereinafter known as precursor specific RNA sequences or psRNA) which are present only in the precursors mRNA, t-RNA, hnRNA or snRNA molecules and not in mature mRNA, R-RNA, t-RNA, hnRNA or snRNA molecules, to detect, identify and quantitate specific organisms, groups or organisms, groups of eukaryotic cells or viruses in cells, by the process of nucleic acid hybridization.

My invention and the novelty, utility and unknown obviousness thereof can be more clearly understood and appreciated when considered in the light of the additional representative background information hereinafter set out, comprising this art:

1. mRNAs, and psRNAs are present in all organisms and cells, hnRNAs and snRNAs are present only in eukaryotic cells. Cell organelles which contain DNA, including mitochondria and chloroplasts, also contain mRNA, psRNA, R-RNA, and t-RNA.
2. A typical bacterial cell contains more than a thousand genes, the vast majority of which code for a specific protein. A mammalian cell contains over 10,000 genes each of which can produce RNA. Any gene has the potential to produce multiple copies of RNA in a cell. Each specific RNA molecule produced is a direct gene product.
3. Many different mRNA sequences can be present in each organism or cell. The individual cells of a multicelled organism may have different mRNA sequences present in each cell or in different groups of cells.

Many different hnRNA, psRNA, and snRNA sequences can be present in each cell or group of cells of a eukaryotic organism.

Cells infected with a specific virus can have present within them a variety of different types of virus specific mRNA and psRNA.

4. The number of copies (hereinafter the abundance) of a specific mRNA in a prokaryotic cell varies from zero to several hundred. The abundance of a specific psRNA sequence in a prokaryotic organism or cell can be 10 to 20 times higher.

The abundance of a specific mRNA molecule in a eukaryotic cell ranges from 1-2 to greater than $10^4$ per cell.

The abundance of a specific hnRNA sequence in a eukaryotic cell ranges from 1-2 to greater than $10^4$ per cell.

The abundance of a specific snRNA molecule in a eukaryotic cell varies from $10^4$ to $10^6$ per cell.

The abundance of a specific psRNA sequence in a eukaryotic cell varies from 1-2 to over $10^4$ per cell.

5. In many eukaryotes, RNA of various types is produced from the repeated sequence fractions of the DNA. This can result in a population of abundant RNA molecules whose sequences are similar but not identical to one another. A probe complementary to one of these RNA molecules will, however, hybridize with all of the other similar RNA molecules.
6. The gene sequences which code for the various individual mRNAs, psRNAs, hnRNAs and snRNAs of viruses and living organisms, have been conserved to varying degrees through evolution. The vast majority of these sequences are much less conserved than t-RNA sequences. SOme of the sequences, however, are highly conserved. For example the gene which codes for histone mRNA is very highly conserved through evolution and the histone gene sequence is quite similar to widely different organisms.

The lack of conservation in the DNA sequences of many of these RNAs allows the production of probes which can readily distinguish between closely related organisms or viruses.

A large number of studies have been done on various mRNAs, hnRNAs, snRNAs and psRNAs (see Gene Expression, Vol. 1 and 2, by B. Lewin, in references). These include hybridization of these RNAs in studies on genetic analysis, regulation and evolution, in prokaryotic and eukaryotic organisms and viruses.

Prior Art Hybridization Procedures

Two basic nucleic acid hybridization procedures are disclosed in the prior art. In one, in solution hybridization, both the probe and sample nucleic acid molecules are free in solution. With the other method the sample is immobilized on a solid support and the probe is free in solution. Both of these methods are widely used and well documented in the literature. An example of the in solution method is presented hereinafter in the examples. Also, in the article by Thomas et al., Proc. Natl. Acad. Sci. USA (1980), 77, p. 520, is an example of the immobilized method.

The basic components of a nucleic acid hybridization test are:

1. Probe—A marked single strand nucleic acid sequence which is complementary to the nucleic acid sequences to be detected (that is the target sequences). As used herein, the target sequence is the total sequence or a sub-sequence of R-RNA, t-RNA, or other RNA.

The probe length can vary from 5 bases to tens of thousands of bases, and will depend upon the specific test to be done. Only part of the probe molecule need be complementary to the nucleic acid sequence to be detected (hereinafter the target sequences). In addition, the complementarity between the probe abd the target sequence need not be perfect. Hybridization does occur between imperfectly complementary molecules with the result that a certain fraction of the bases in the hybridized region are not paired with the proper complementary base. A probe may be composed of either RNA or DNA. The form of the nucleic acid probe may be a marked single strand molecule of just one polarity or marked single strand molecule having both polarities present. The form of the probe, like its length, will be determined by the type of hybridization test to be done.

2. Sample—The sample may or may not contain the target molecule (i.e. the organism of interest). The sample may take a variety of forms, including liquid such as water or serum, or solid such as dust, soil or tissue samples. The sample nucleic acid must be made available to contact the probe before any hybridization of probe and target molecule can occur. Thus the organism's RNA must be free from the cell and placed under the proper conditions before hybridization can occur. Prior art methods of in solution hybridization necessitate the purification of the RNA in order to be able to obtain hybridization of the sample R-RNA with the probe. This has meant that to utilize the in solution method for detecting target sequences in a sample, the nucleic acids of the sample must first be purified to eliminate protein, lipids, and other cell components, and then contacted with the probe under hybridization conditions. The purifications of the sample nucleic acid takes at least several hours and can take up to a day, depending on the nature and quantity of the sample.

3. Hybridization Method—Probe and sample must be mixed under conditions which will permit nucleic acid hybridization. This involves contacting the probe abd sample in the presence of an inorganic or organic salt under the proper concentration and temperature conditions. The probe and sample nucelic acids must be in contact for a long enough time that any possible hybridization between the probe and sample nucleic acid may occur.

The concentration of probe or target in the mixture will determine the time necessary for hybridization to occur. The higher the probe or target concentration the shorter the hybridization incubation time needed.

A nucleic acid hybridization incubtation mixture composed of probe and sample nucleic acids must be incubated at a specific temperature for a long enough time for hybridization to occur. The length of time necessary for hybridization to complete depends upon the concentration of the probe nucleic acid, the concentration of the sample nucleic acid which is complementary to the probe, and a basic rate of hybridization which is characteristic of the hybridization conditions used. The basic rate of hybridization is determined by the type of salt present in the incubation mix, its concentration, and the temperature of incubation. Sodium chloride, sodium phosphate and sodium citrate are the salts most frequently used for hybridization and the salt concentration used is rarely above 1M and sometimes as high as 1.5–2M. The salts mentioned above yield comparable rates of nucleic acid hybridization when used at the same concentrations and temperatures, as do the comparable potassium, lithium, rubidium, and cesium salts. Britten et al. (1974) (Methods in Enzymology, Volume XXIX, part E., ed. Grossman and Moldave; Academic Press, New York, page 364) and Wetmur and Davidson (1968) (J. Molecular Biology, Vol. 31, page 349) present data which illustrates the standard basic rates of hybridization attained in commonly used salts. The hybridization rates of DNA with RNA vary somewhat from those of DNA hybridizing with DNA. The magnitude of the variation is rarely over tenfold and varies, depending for example, on whether an excess of DNA or RNA is used. See Galau et al. (1977) (Proc. Natl. Acad. Sci. USA, Vol 74, #6, pg. 2306).

Certain conditions result in the acceleration of DNA;DNA hybridization. An emulsion of phenol and salt promotes the very rapid hybridization of DNA when the mixture is agitated. Rate increases several thousand times faster than standard DNA hybridization rates are attained with this system (Kohne et al., Biochemistry (1977) Vol. 16, p. 532a). DNA hybridization rate acceleration fo 50 to 100 fold over the standard rates has also been observed when neutral and anionic dextran polymers were mixed with single strand DNA in solution (Wetmur, Biopolymers (1975) Vol 14, p. 2517). Neither of these DNA accelerated rate condtions was reporter to accelerate the hybridization rate of DNA:RNA hybridization. I am not aware of any prior art which documents a condition for accelerating the rate of RNA:DNA hybridization.

4. Hybridization Assay—A procedure is need to detect the presence of probe molecules hybridized to the target molecules. Such a method depends upon the ability to separate probe which is hybridized to target molecules from probe which is not hybridized to target molecules. Prior art procedures for assaying in solution hybridization mixtures have been done on sample nucleic acids which are first purified and then contacted with the prove in the hybridization incubation mixture.

Hydroxyapatite (HA) has been used as a standard method for assaying in solution hybridization mixtures for the presence of hybridized probe. Under the proper conditions HA selectively binds hybridized DNA probe but does not bind probe which is not hybridized. Other methods are available to assay for hybridized probe. These include $S_1$ nuclease assay which depends on the ability of a specific enzyme to degrade non-hybridized probe to small subunits while the hybridized probe is not degraded by the enzyme and remains large. The degraded probe can then be separated from the hybridized probe by a size separation technique. Various methods for assaying for in solution hybridized nucleic acids are presented in Britten et al. (1974) supra.

The immobilized sample nucleic acid hybridization methods have the hybridization assay built into the hybridization method. These methods involve fixing the sample nucleic acid onto an inert support and then hybridizing this immobilized nucleic acid with a marked probe which is free in solution. Hybridization of any probe with the immobilized sample nucleic acid results in the binding of the probe to the sampel nucleic acid and therefore the attachment of the probe to the inert support. Non-hybridized probe remains free in solution and can be washed away from the inert support and the hybridized probe. Such a method requires at least several hours to prepare the sample for nucleic acid hybridization and one to two hours of washing and utilizes large amounts of probe. An advantage of this method is the capability to place multiple samples on the same inert support and to hybridize and process all the samples at one time. Examples of such an immobilized sample method is presented in Analytical Biochemistry (1983) Vol. 128, p. 415, and J. of Infectious Disease (1982) Vol. 145, #6, p. 863.

Making Nucleic Acids Available for Hybridization

In solution nucleic acid hybridization methods have always utilized nucleic acids which have been purified away from other cell components. Nucleic acids in cells and viruses are normally tightly complexed with other cell components, usually protein, and, in this form are not available for hybridization. Simply breaking the cell or virus open to release the contents does not render the nucleic acids available for hybridization. The nucleic acids remain complexed to other cell or viral components even though released from the cell, and may in fact become extensively degraded by nucleases which also may be released. In addition a marked probe added to such a mix may become complexed to "sticky" cell or viral components and be rendered unavailable for hybridization, or the probe may be degraded by nuclease action.

A variety of prior art methods exist for purifiying nucleic acids and several of these are described in Maniatis et al., supra. These methods are all time consuming—one taking an hour is regarded as very rapid—and require multiple manipulations.

Insofar as I am aware, there is no prior art method for performing in solution nucleic acid hybridization which does not require the use of some sort of pre-purification step to make the nucleic acids available for hybridization.

The immobilized nucleic acid hybridization methods involve fixing the sample nucleic acid onto an inert support and then hybridizing this immobilized nucleic acid with marked probe which is free in solution. The process of fixing the nucleic acids on the intert support provides a purification step effective enough to make the bound nucleic acids available for hybridization. Most of the non-nucleic acid cell or viral components do not bind to the inert support, and those which do bind do so at a different location than the nucleic acids. Such a method requires several hours, at a minimum, to prepare the sample nucleic acids for hybridization. An advantage of this method is the ability to place multiple samples on the inert support and process them all together through the hybridization and the hybridization assay steps. The hybridization assay consists of removing the inert support from the hybridization mixture. Prove which is hybridized to the fixed sample remains with the intert support while non-hybridized probe remains free in solution.

Thus, while the presence of organisms can be detected by any one of a large variety of prior art methods, none of these is entirely satisfactory for one reason or another. Such methods include, e.g., growth methods, optical detection methods, serologic and immunochemical methods, and biochemical methods, as shown below:

Growth Tests:

A large number of different growth tests exist, each useful for the growth of a specific organism or group of organisms. Growth tests have the potential sensitivity to detect one organism. In practice, however, many organisms are difficult or impossible to grow. These tests are usually lengthy, taking from one day, to months, to complete. In addition, a very large number of tests would be needed to detect the presence of any member of a large group of organisms (e.g., all bacteria), assuming that the growth conditions for all members of the group are known.

Optical Detection Methods:

Microscopic analysis coupled with differential staining methods is very powerful, and in many cases, very rapid detection method. A major problem with this approach is the detection of specific organisms in the presence of large quantities of other organisms, for example, the identification of a specific type of gram negative rod shaped bacteria, in the presence of many different kinds of gram negative rod shaped bacteria. In addition, a large number of tests would be needed to detect the presence of all members of a large group of organisms (such as the group of all bacteria).

Serologic and Immunochemical Methods and Biochemical Tests:

A large number of different types of these tests exist. They are usually qualitative, not very sensitive and often require a growth step. A great many of these tests would be required to detect all members of a large group of organisms.

U.S. Pat. No. 4,358,535 to Falkow et al. discloses a method for the detection of genetic material, i.e., Genes or Genomes. In this patent a clinical sample or isolate suspected of containing a pathogen is transferred onto an inert porous support, such as a nitrocellulose filter, and treated in such a way that the cells are localized. The cells are then treated in such a way as to release their DNA and case it to couple onto the support. Subsequent treatment causes a separation of the individual DNA strands of the genome. The strands are then contacted with labeled probes specific for the characteristic polynucleotide sequence under hybridization conditions. Hybridization of the probe to the single stranded polynucleotides from the pathogen is detected by means of the label.

The method of this patent, for detecting genes or genomes, like the other methods mentioned above does not have the specificity, sensitivity, rapidity or ease of performance of that of my invention. A summary of comparisons of the Falkow et al. method as disclosed in the patent and that of applicant's method, as herein disclosed, is set out below:

| | FALKOW ET AL. METHOD | APPLICANT'S METHOD |
|---|---|---|
| 1. Method of doing hybridization | Immobilized method only | In Solution method emphasized. Immobilized method can be used. |
| 2. Class of nucleic acid to be detected | Genetic material (i.e., Genes or Genomes). In cellular organisms the genetic material is always DNA. | Detection of a primary gene product (RNA) only. RNA is not present as genetic material in cellular organisms. |
| 3. Abundance (copies per cell) of nucleic acid sequences to be detected | Virtually all microorganism chromosomal genes are present only one time per cell. Extrachromosomal genes are ususally present 1–3 times per cell. Ribosorial RNA genes are present 3–6 times per cell. | $10^4$ copies of R-RNA are present per bacterial cell. About 2 × $13^3$ copies of each t-RNA is present in each bacterial cell. Ten to 200 of each specific mRNA molecule is present per bacterial cell. The numbers are generally higher in eukaryotic cells. |
| 4. Ability of hybridization method to quantitate nucleic acids | None disclosed | Excellent ability to quantitate nucleic acids, both DNA and RNA. |
| 5. Ability to determine and quantitate the state of genetic expression of a cell | Genetic expression cannot be determined by detecting genetic material. | Genetic expression can be determined and quantitated by using probes which detect the primary gene products or RNAs. |
| 6. Relative probability of detecting a false positive during diagnosis | High (detects only specific genes). | Low (when emphasis on detecting RNA). |
| 7. Relative sensitivity of detection of nucleic acids | Good. Nucleic acid hybridization test are in general quite sensitive. | Highly sensitive. From 20 to $10^4$ times more sensitive than possible with the approach outlined in Falkow. RNA is almost always more abundant than the genes which make it. The in solution method also confers extra sensitivity over the immobilized method. |
| 8. Preparation of sample for hybridization test | Takes from 2–10 hours to immobilize sample nucleic acids and make them available for hybridization. Includes a step for converting DNA to single strand form. Not all the sample nucleic acids are capable of hybridization. | Takes 1–5 minutes to make sample available for hybridization. RNA in cells is already single stranded. All of the sample nucleic acid is capable of hybridizing. |
| 9. Amount of probe needed | Usually takes 0.01 to 1 micrograms of probe in hybridization texture. | Need $10^{-5}$ to $10^{-6}$ micrograms of probe per sample. |
| 10. Time needed for hybridization to occur | 2–20 hours | 0.2–0.6 hours |

I am not aware of any prior art which teaches my method of detecting the presence or absence of R-RNA, or of t-RNA characteristics of a particular group of organisms utilizing nucleic acid hybridization wherein is used a selected mearked nucleic acid molecule complementary to a subsequence of R-RNA from a particular source. Nor am I aware of any prior art which discloses my method for detecting the presence or absence of R-RNA in general, or of t-RNA from a particular source, by nucleic acid hybridization using a marked nucleic acid molecule complementary to all of the R-RNA, or t-RNA subsequences from a specific source.

Nor am I aware of any prior art which teaches my method of detecting the presence or absence of specific sequences or populations of different specific sequences of mRNA, psRNA, hnRNA or snRNA to detect, identify and quantitate specific organisms, groups of organisms, groups of eukaryotic cells, or specific viruses in cells or a group of specific viruses in cells, by nucleic acid hybridization wherein is used selected marked nucleic acid molecules complementary to a subsequence(s), a sequence(s) or a population of sequences of subsequences of mRNA, hnRNA, snRNA or psRNA from a particular source.

Nor am I aware of any prior art which teaches my method of detecting the presence or absence of a nucleic acid characteristic of a particular group of organisms or viruse; or of rapidly making available for in solution nucleic acid hybridization with a specific marked probe, the nucleic acids of a particular group of organisms or viruses for any purpose; or of utilizing an in solution nucleic acid hybridization method which combines a rapid method for making the nucleic acids of specific groups of organisms available for hybridization with a specific complementary probe, with a method for detecting an organism's nucleic acid by greatly accellerating the rate of in solution hybridization of the nucleic acids of an organim or virus and the marked probe complementary to the organism's or virus's nucleic acid; or of determining the antimicrobial agent sensitivity or antiviral agent sensitivity of a particular group of organisms or viruses; or of assaying for the presence of antimicrobial or antiviral substances in blood, urine, other body fluids or tissues or other samples; or for determining the state of growth of cells; or of detecting microorganism or virus infections; or of rapidly assaying for the presence, in a hybridization mixture, of probe which has hybridized, by contacting the mixture with hydroxyapatite under predetermined conditions and then processing the resulting solution in a specific manner.

DISCLOSURE OF THE INVENTION

The present invention provides a method and means for detecting, identifying, and quantitating organisms in biological and other samples, and more particularly to a method for specifically and sensitively detecting and quantitating any organism containing the ribosomal RNA, (hereinafter R-RNA), transfer RNA (hereinafter t-RNA) or other RNA, any members of large, intermediate, or small size categories or taxonomic groups of such organisms; and previously unknown organisms containing R-RNA or t-RNA. The method is capable of detecting the presence of even one organism, containing R-RNA or t-RNA.

The invention also provides a method for using specifically produced nucleic acids complementary to specific sequences or populations of different sequences of the RNA class mRNA, or hnRNA, or snRNA, or the class of RNA sequences (hereinafter precursor specific RNA sequences or psRNA) which are present only in the precursor mRNA, R-RNA, t-RNA, hnRNA or snRNA molecules, and not in mature mRNA, t-RNA, hnRNA or snRNA molecules, to detect, identify, and quantitate specific organisms, groups of organisms, groups or eukaryotic cells or viruses in cells.

The invention also provides a method and means having as characterizing qualities: (a) the ability to specifically detect the presence of any one of a large number of different organisms with a single assay procedure which also works regardless of the pattern of genetic expression of any particular organism; (b) the ability to modify the test to detect only specific categories of organisms, even in the presence of organisms not in the group of interest; (c) extremely high sensitivity of detection, and ability to detect the presence of one organism or cell; (d) the ability to quantitate the number of organisms or cells present; and (e) does not require a growth step.

My invention provides means for detecting the antimicrobial agent sensitivity or antiviral agent sensitivity of a particular group of organisms or viruses; for assaying the presence of antimicrobila or antiviral substances in blood, urine, other body fluids or tissues or other samples; for determining the state of growth of cells; for detecting microorganisms or virus infections; and for rapidly assaying for the presence in a hybridization mixture of probe which has hybridized.

As described hereinbefore, R-RNA base sequences are partially similar in widely different organisms. The more closely related two organisms are, the larger the fraction of the total R-RNA which is similar in the two species. The R-RNA sequence of any particular species or organism can be regarded as a series of short R-RNA subsequences, of which one subsequence is similar in virtually all life forms. Therefore, the R-RNA of almost all life forms must contain this subsequence. A different subsequence is similar only in the R-RNA of the members of the Species to which that organism belongs. Other subsequences are present in the Order or organisms that the Species belongs to, and so on.

Because the R-RNA sequences of widely different organisms are at least partially similar, the method of my invention, using a probe which detects the R-RNA sequences which are similar in widely different organisms, can detect the presence or absence of any one or more of those organisms in a sample. A marked nucleic acid sequence, or sequences complementary to the R-RNA sequences similar in widely divergent organisms, can be used as such a probe in nucleic acid hybridization assay.

Because of the R-RNA sequences of closely related organisms are more similar than those of distantly related organisms, the method of my invention, which includes using a probe which detects only the R-RNA sequences which are similar in a particular narrow group or organisms, can detect the presence or absence of any one or more of those particular organisms in a sample, even in the presence of many non-related organisms. These group specific probes can be specific for a variety of different sized categories. One probe might be specific for a particular taxonomic Genus, while another is specific for a particular Family or another Genus.

Group specific probes have the ability to hybridize to the R-RNA of one group or organisms but not hybridize to the R-RNA of any other group of organisms. Such a group specific complementary sequence will detect the presence of R-RNA from any member of that specific group of organisms even in the presence of a large amount of R-RNA from many organisms not belonging to that specific group.

The total number of R-RNA molecules in a sample is measured by using a marked sequence or sequences complementary to R-RNA and standard excess probe or excess sample RNA nucleic acid hybridization methodology.

The R-RNA content of cells from a wide variety of organisms is known in the art. In a broad group of similar organisms, for example bacteria, the amount of R-RNA per cell varies roughly 2–5 fold. Therefore, if the number of R-RNA molecules in a sample, and the broad class identity of the source of the R-RNA is known, then a good estimate of the number of cells present in the sample can be calculated. If the broad class identity is not known it can be determined by hybridizing the sample to a series of selected probes complementary to R-RNA, each of which is specific for a particular broad category of organisms.

At the present time, the operational detection and quantitation range of a single assay procedure is from $10^4$ R-RNA molecules (1 bacterium or $10^{-2}$ mammailan cells) to about $10^{12}$ R-RNA molecules ($10^8$ bacteria or $10^6$ mammalian cells) a span of about $10^8$ in cell numbers. A single test could also be done in such a way as to operationally quantitate from $10^3$ bacteria to $10^{10}$ bacteria. The test is quite flexible in this way.

Because the test for R-RNA is specific and has the ability to detect the presence of very few organisms there is no need to amplify the numbers of organisms through a growth step.

The practice of that form of my invention which is directed to determining the presence of an organism which contains R-RNA, in a sample which might contain such organism, comprises basically:

a) bringing together the sample, or isolated nucleic acids contained in that sample, with a probe which comprises marked nucleic acid molecules which are complementary to the R-RNA of all organisms;

b) incubating the resulting mixture under predetermined hybridization conditions for a predetermined time, and then;

c) assaying the resulting mixture for hybridization of the probe.

When my invention is directed to determining the presence of any member of a specific category of organisms which contain R-RNA in a sample which might contain such organisms, the method comprises:

a) contacting the sample, or the nucleic acids therein, with a probe comprising marked nucleic acid molecules which are complementary only to the R-RNA of members of the specific category or organisms, but not complementary to R-RNA from non-related organisms;

b) incubating the probe and the sample, or the isolated nucleic acids therein; and c) assaying the incubated mixture for hybridization of said probe.

My invention can also be used to determine the number of organisms present in the sample under investigation, by adding to the assying in the second above described method in the event probe hybridization has occurred, the step of comparing the quantity of R-RNA present in the sample with the number of R-RNA molecules normally present in individual organisms belonging to the said specific group.

And, of course, included in the variations, within the scope of my invention, which can be used, is that which comprises, in lieu of the single probe of step (a) in the second of the above methods, a multiplicity or battery, of different probes. In such case, each separate probe comprises marked nucleic acid molecules which are complementary only to the R-RNA of a specific group of organisms and each probe is specific for a different group of organisms; step (a) is followed by incubating each probe-sample mixture under predetermined hybridization conditions for a pre-determined time, and then assaying each mixture for hybridization of the probe.

As described hereinbefore t-RNA base sequences are partially similar in widely different organisms. The more closely related two organisms are the larger the fraction of t-RNA sequences which are related. Each t-RNA gene sequence can be regarded as a series of short t-RNA subsequences. One subsequence is similar in a large related group of organisms. Another subsequence is similar in an intermediate sized related group of organisms while a third subsequence is similar in a small related group of organisms and so on.

Since, also, the t-RNA sequences of widely different organisms are at least partially similar, the method of my invention, using a probe which detects the t-RNA sequences which are similar in widely different organisms, can detect the presence or absence of any one or more of those organisms in a sample. Thus, a marked nucleic acid sequence, or sequences complementary to the t-RNA sequences similar in widely divergent organisms, can be used as such a probe in a nucleic acid hybridization assay.

And since the t-RNA sequences of closely related organisms are more similar than those of distantly related organisms, the method of my invention, which includes using a probe which detects only the t-RNA sequences which are similar in a particular narrow group of organisms, can detect the presence or absence of any one or more of those particular organisms in a sample, even in the presence of many non-related organisms. Such group specific probes can be specific for a variety of different sized categories. For example, one probe might be specific for a particular taxonomic Genus, while another is specific for a particular Family or another Genus.

Group specific probes have the ability to hybridize to the t-RNA of one group of organisms but not hybridize to the t-RNA of any other group of organisms. Such a group specific complementary sequence will detect the presence of t-RNA from any member of that specific group of organisms even in the presence of a large amount of t-RNA from many organisms not belonging to that specific group.

In the practive of that form of the invention which is directed to determining the presence of any member of a specific category of organisms which contain t-RNA in a sample which might contain such organisms, the method comprises:

a) contacting the sample, or the nucleic acids therein, with a probe comprising marked nucleic acid molecules which are complementary only to the t-RNA of members of the specific category of organisms, but not complementary to t-RNA from non-related organisms.

b) incubating the probe and the sample, or the isolated nucleic acids therein; and c) assaying the incubated mixture for hybridization of said probe.

My invention can also be used to determine the number of organisms present in the sample under investigation, by adding to the assying in the second above described method in the event probe hybridization has occurred, the step of comparing the quantity of t-RNA present in the sample with the number of t-RNA molecules normally present in individual organisms belonging to the said specific group.

And, of course, included in the variations, within the scope of my invention, which can be used, is that which comprises, in lieu of the single probe of step (a) in the second of the above methods, a multiplicity or battery, of different probes. In such case, each separate probe comprises marked nucleic acid molecules which are complementary only to the t-RNA of a specific group of organisms and each probe is specific for a different group of organisms; step (a) is followed by incubating each probe-sample mixture under predetermined hybridization conditions for a pre-determined time, and then assaying each mixture for hybridization of the probe.

The method and measn of my invention are more fully illustrated in the following description of characterizing features of test methods in accordance with the invention.
Nucleic Acid Hybridization Test Procedures for Detecting and Quantitating RNA A desirable detection test should: a) be rapid; b) be easy to use; c) be highly sensitive; d) be able to detect and quantitate in just one lab assay.

The existent of a nucleic acid probe which will hybridize to R-RNA from any member of the Genus Legionella, but does not hybridize to R-RNA from any other source, makes possible a rapid, easy to use, sensitive, in solution detection test which can both detect and quantitate, for example, Legionella bacteria with the performance of just one laboratory assay and does not require the purification of nucleic acids from the sample.

A description of the basic aspects of this in solution hybridization test procedure follows. While the procedure described is designed for detecting members of the Genus Legionella, it is obvious that this same test procedure can be used with the appropriate probe to detect many other groups or organisms or viruses.

Step 1. Preparing the Sample

Mix the sample with a solution containing a detergent and a proteolytic enzyme. The detergent lyses the bacteria and helps solubilize cellular components while the enzyme destroys the cellular proteins, including those enzymes which degraded RNA and DNA. The composition of the detergent-enzyme mix depends upon the type of detergent and proteolytic enzyme used and the amount and type of sample to be checked. Detergents used include sodium lauryl sulfate, sarkosyl and Zwittergent, while the enzymes used include Proteinase K and Pronase. A wide variety of enzymes, solubilizing agents such as chaotropic agents, can be used. The probe can also be present in the detergent-enzyme mix added to the sample.

The enzyme-detergent acts very quickly on any Legionella bacteria in the sample. In most cases it is not necessary to incubate the mixture in order to make the R-RNA available for in solution hybridization with the probe. In certain cases a short incubation period is needed.

In other situations it is not necessary to include the proteolytic enzyme, and detergent alone will make the R-RNA available for in solution hybridization with the probe.

This approach provides a very rapid and easy method for getting the sample R-RNA into a state where it can hybridize with the probe in an in solution assay. In addition, it allows the hybridization to occur in solution without purifying the sample R-RNA. A key to this method is that the probe detects Legionella R-RNA. R-RNA is single stranded in the cell and ready to hybridize with the probe once the ribosomal proteins are removed from the R-RNA. In contrast, to directly detect the ribosomal R-RNA DNA (i.e., the gene for R-RNA) or any other DNA sequence it would be necessary to add a procedure which caused the double stranded R-RNA gene to separate into two single strands before the probe could hybridize to it.

To the best of my knowledge, there is no prior art concerning the use of an enzyme-detergent-sample method for making R-RNA, transfer R-RNA, RNA in general or DNA available for in solution hybridization with a probe for the purpose of detecting and quantitating the presence or absence of organisms in general or a specific group of organisms.

Step 2. Preparing the Hybridization Incubation Mixture

To the sample-enzyme-detergent mix add the probe and sufficient salt to enable hybridization to occur and incubate the resultant mixture at an appropriate temperature. The salt concentration and the temperature of hybridization incubation combine to determine the criterion. The criterion of the incubation condition must be equal to that used to select the probe or the specificity of the probe may change.

The incubation mixture must be incubated for a long enough time for hybridization to occur. The salt type and concentration determines the rate of hybridization which can be attained. Thus, certain salts will promote very rapid hybridization when used at the proper concentration. An example of such a salt is sodium phosphate. Legionella specific probe mixed with purified Legionella R-RNA in 3.0M sodium phosphate buffer (pH=6.8) (hereinafter termed PB) and incubated at 76° C. hybridizes over 100 times more rapidly than the same amounts of Legionella probe and R-RNA incubated under standard conditions of 0.72M NaCL, 76° C. (these two conditions are equal in criterion). Other salts can also be used to effect this hybridization rate acceleration. These include most sodium, ammonium, rubidium, potassium, cesium, and lithium salts.

In 3M PB at 76° C. the hybridization rate of the Legionella specific probe with Legionella R-RNA present in the PB-enzyme-detergent-sample probe mixture is also accelerated by over 100 times over the hybridization rates seen for the standard incubation conditions. Hybridization also occurs between the probe and R-RNA in an enzyme-detergent-sample mixture under standard salt concentration conditions.

One of the features of the invention, as previously pointed out, is the ability to detect very small numbers of organisms by detecting their R-RNA. This is possible because of the large numbers of R-RNA molecules in each cell. In Legionella-like organisms 5,000 to 10,000 R-RNA molecules are present in each individual bacterial cell. One of the major determinants of the sensitivity of detection which can be achieved with nucleic acid hybridization is the rate of hybridization which can be attained. The combination of detection of R-RNA and the use of the rate accelerating incubation conditions described above make it possible to attain extremely high sensitivity of detection of bacteria and other organisms in a very short period of time with the use of very small amounts of sample and probe. An illustrative example of this is described later.

To the best of my knowledge there is no prior art concerning the use of rate-accelerating systems with in solution hybridization tests for determining the presence or absence of an organism or group of organisms by detecting the R-RNA, transfer RNA, other RNA or DNA of the organisms of interest. There is also no prior art of which I am aware concerning the use of a combination of a rate-accelerating system and the enzyme-detergent-sample-probe mixtures to determine the presence or absence of a specific organism or virus or group of organisms or viruses by detecting the R-RNA, transfer RNA, or other RNA or DNA of the specific organism or group of organisms of interest.

Step 3. Assaying the Incubation Mixture for Hybridization of the Probe with Target R-RNA The signal that the sample contains the target R-RNA molecules (and therefore the target organism) is the presence of hybridized probe in the incubation mixture. Thus the incubation mixture must be assayed for the presence of hybridized probe at the end of the incubation period. It is desirable that such an assay be easy to perform and rapid. For this assay the incubation mix is processed by utilizing hydroxyapatite (HA). Under the proper conditions HA binds R-RNA rapidly and completely but does not bind the non-hybridized probe molecules. If a probe molecule is hybridized to a target R-RNA molecule the probe also binds to the HA because it is physically attached to the R-RNA.

Detection of organisms by detecting their R-RNA is a feature of the invention. The ability of the HA to bind R-RNA or RNA in general, in seconds, while not binding the probe at all, has allowed the development of a hybridization assay method which takes minutes to perform, has great flexibility and which adapts well for handling multiple samples. In addition the sample-detergent-enzyme-probe incubation mixture, can be diluted into the appropriate buffer and directly processed to assay for the presence of hybridized probe.

HA is known in the art as a substance used for assaying hybridization of probes. The assay method described here, which has great advantages over the prior art uses of HA (Brenner et al., Analytical Biochm (1969(28 p. 477), can be carried out at room temperature and will work over a temperature range of about 15° C. to about 90° C. It has fewer steps and does not require heating at each centrifugation step; it can be carried out in the presence or absence of detergents such as Zwittergent (Calbiochem, San Diego, Calif.) and sodium lauryl sulfate. It is 3–5 times faster, and a single assay can be done in 3–5-minutes. It requires about 5 times less HA. Detergent concentration can range from 0 to 10%, while the phosphate concentrations can range from 0.1M to 0.2M depending on the type of assay. The method can also be readily adapted for handling multiple samples.

Methods other than HA are available to assay for hybridization of the probe. These include enzyme assays such as the $S_1$ enzyme method, size separation methods, and a variety of sample immobilization methods. The probes discussed here can be used effectively with these and any other method of conducing hybridization and hybridization assays.

Procedures for the Production of Group Specific R-RNA Probes

Different approaches can be used to produce group specific probes. All of these approaches but one, rely on differential nucleic acid hybridization methods to identify and purify the group specific probe sequences.

Procedure A:

The most useful procedure for producing group specific R-RNA probes uses recombinant DNA methodology. The steps involved in this procedure follow: (The specific details of standard DNA recombinant techniques are described in the book, *Molecular Cloning, A Laboratory Manual*, T. Maniatis et al., Cold Spring Harbor Publication (1982))

1. Isolate nucleic acid from a specific organism of interest. Standard isolation methods are used.
2. Using this isolated DNA, clone the R-RNA genes of this organism and then produce large amounts of the ribosomal gene DNA, using standard DNA recombinant technology, as shown in Maniatis et al., supra.
3. Reduce the R-RNA gene DNA to short pieces with restriction enzymes and make a library of these short DNA pieces, using standard DNA recombinant methods, as shown in Maniatis et al., supra.
4. Screen the library and identify a clone which contains a short R-RNA gene sequence which hybridizes only to R-RNA from other members of the taxonomic Species of the organism of interest. Isolate this clone. It contains a Species specific DNA sequence which is complementary only to the R-RNA of the specific Species to which the organisms of interest belongs.

Screen the library further and identify and isolate the following clones: a) a clone which contains a DNA sequence complementary to R-RNA which will only hybridize to R-RNA from members of the taxonomic Genus to which the organism of interest belongs; b) a clone which contains a DNA sequence complementary to R-RNA which will only hybridize to R-RNA from members of the taxonomic Order to which the organism of interest belongs; c) a clone which contains a DNA sequence complementary to R-RNA which will hybridize only to R-RNA from members of the taxonomic Family to which the organism of interest belongs; d) a clone which contains a DNA sequence complementary to R-RNA which will hybridize only to R-RNA from members of the taxonomic Class to which the organism of interest belongs; and e) a clone which contains a DNA sequence complementary to R-RNA which will hybridize to R-RNA from as many different life forms as possible.

The foregoing clone selection scheme is only one of a member of possible ones.

Standard methods of cloning and screening are to be utilized, as discussed in Maniatis et al., supra.

5. a) Produce large amounts of each clone's DNA. From the DNA of each individual clone isolate and purify only the DNA sequence which is complementary to R-RNA, using one of the many methods existing to accomplish this, e.g., as in Maniatis et al., supra.
b) In certain instances the total DNA present in a clone is useful as a probe, in which case the total DNA isolated from the cloning vector is used.
c) In certain other instances, the DNA single strand of the cloning vector which contains the DNA sequence complementary to R-RNA is used as a probe. In such case this strand must be isolated and purified, using one of the various methods which exist to accomplish this, as described by Maniatis et al.
d) The probe DNA obtained in 5a, 5b, and 5c must be marked in some way so that it can be identified in the assay mixture. Many different kinds of markers can be used, the most frequently used markder being radioactivity. Others include fluorescence, enzymes, and biotin. Standard methods are used for marking the DNA, as set out in Maniatis et al., supra.

7. The group specific R-RNA gene sequence in the cloning vector exists in a double strand state. One of these strands is complementary to R-RNA and will hybridize with it. The other strand will not hybridize to R-RNA but can be used to produce marked group specific sequences complementary to R-RNA. This is done by utilizing a DNA or RNA polymerase and nucleic acid precursor molecules which are marked. The enzyme will utilize the marked precursors for synthesizing DNA or RNA using the DNA strand as a template. The newly synthesized marked molecule will be complementary to R-RNA and can be used as a group specific probe. The template DNA can be removed by various established means leaving only single strand marked nucleic acid, as described in Maniatis, et al., supra, and the article by Taylor et al., in Biochemics and Biophys. Acta (1976) 442, p. 432.

Procedure B:

Several enzymes can utilize a R-RNA from any source as a template for the synthesizing of marked DNA complementary to the entire R-RNA sequence. Group specific sequences complementary only to the R-RNA of a particular class of organisms can be isolated by a hybridization selection process. The fraction of the synthesized marked DNA which hybridizes only to the R-RNA from members of a specific class of organisms can be isolated by standard hybridization procedures. An example of this process is presented hereinafter. Such a probe can be produced in sufficient quantities to clone as is described in A. The base sequence of this clone can be determined by standard methods and the sequence used to direct the production of the probe by chemical synthesis using standard methods.

Procedure C:

The nucleotide sequences of R-RNA from widely different organisms have been determined. Group specific sequences similar to a specific group of organisms can be identified by comparing these known sequences. A sequence complementary to this group specific R-RNA sequence can then be chemically synthesized and marked, using standard methodology.

Production of Specific Probes Complementary to t-RNA

While different approaches can be used to produce specific t-RNA probes, the same basic approaches described for producing R-RNA probes can be used to produce t-RNA probes. Standard methods are available to isolate individual t-RNA species and genes and these are well known in the art. The form of the probe may be DNA or RNA, and the length of the probe may be 12 to thousands of bases long. The probe need not be perfectly complementary to the nucleic acid it is specific for, i.e., the target nucleic acid, and the whole length of the probe need not be complementary to the target molecule.

Production of Specific Probes Complementary to mRNA, hnRNA, snRNA or psRNA

The same basic approaches used to produce specific probes complementary to R-RNA can be used to produce specific probes for specific classes or populations of mRNA, hnRNA, snRNA, or psRNA. The methods for isolating each class of RNA and further fractionating it are well known in the art. Again the form of the probe may be DNA or RNA, and the length of the probe may vary from about 12 to thousands of bases long. The complementary region of the probe need not be perfectly complementary to the target nucleic acid and the whole length of the probe need not be complementary to the target molecule.

Isolating Sample Nucleic Acid

Standard prior art methods can be used to isolate nucleic acid from the samples to be assayed. One standard method of nucleic acid isolation and purification is presented in the examples section and is also discussed in Maniatas et al., supra.

A new technique for making nucleic acids available for in solution hybridization without performing a purification step is described hereinafter.

Performing the Nucleic Acid Hybridization

An appropriate amount of marked probe is mixed with the sample nucleic acid. This mixture is then adjusted to a specific salt concentration (NaCl is usually used) and the entire mix incubated at a specific temperature for a specific time period. At the end of the time period the mixture is analyzed by performing a hybridization assay. Many different combinations of salt, solvent, nucleic acid concentrations, volumes, and temperatures exist which allow nucleic acid hybridization. The preferred combination depending on the circumstances of the assay. It is important, however, that the criterion (see "Definitions") of the hybridization steps be identical to criteria used to identify and select the group probe. If the criteria of the hybridization step is different, the probe specificity may change. See: "Repeated Sequences in DNA", by Britten and Kohne, Science (1968) 161 p. 529; "Kinetics of Renaturation of DNA", by Wetmur and Davidson, J. Mol. Biol. (1968) 31 p. 349; "Hydroxyapatite Techniques for Nucleic Acid Reassociation", by Kohne and Britten; Procedures in Nucleic Acid Research (1971), eds. Cantoni and Davies, Harper and Row, Vol 2, p. 500.

Two different approaches are used with regard to the amount of probe and sample nucleic acid present in the hybridization mixture. In one, the excess probe method, there is more probe present than sample nucleic acid, in this case RNA. With the other, the excess RNA method, there is more R-RNA present than probe. The excess probe method is the method of choice for detecting the presence of RNA in unknown samples. It has several advantages which are discussed below. See Tables 1 and 2 for further discussion of these two approaches.

Using the excess probe method, the detection and quantitation can be done with just one lab assay point, if the proper RNA prone is available. If the hybridization has gone to completion the amount of probe which has hybridized is a direct measure of the amount of RNA present in the sample. The fact that the probe hybridizes at all indicates that RNA is present, and the amount of probe which hybridizes indicates the amount of RNA present in the sample.

Making sure that the hybridization has gone to completion in a known time is important in order to quantitate the RNA. This is readily done by adding enough probe to ensure that the hybridization goes to completion in a selected time period. The more probe added, the faster completion is reached. Thus the excess probe method provides a means to ensure that the hybridization has gone to completion and to know when this has occurred.

In contrast, the detection and quantitation of RNA can't be done with one lab assay point when using the excess R-RNA method. In addition, the time when the test point should be taken cannot be predicted in the excess RNA method. Unknown samples with small amounts of RNA will hybridize much more slowly than samples with large amounts of RNA.

The Assay for Hybridization

The signal that RNA of the specific group is in the sample is the presence of double strand marked probe. Many different methods, well documented in the literature, are available for assaying the hybridization mixture for the presence of marked probe in the double strand form. The choice of method depends upon the method chosen for the hybridization step, the composition of the hybridization mixture, the type of marker on the probe and other factors. One commonly used method is described hereinafter. See also Wetmur and Davidson, Kohne and Britten, and Thomas et al., supra. Also the article by Flavell et al., Eur. J. Biochem. (1974) 47 p. 535. And also, the article by Maxwell et al., Nucleic Acids Research (1978) 5 p. 2033.

In all cases, however, it is important to either assay at or above the same criterion used for the hybridization reaction or at a criterion at which hybridization cannot occur.

Quantitation of Nucleic Acid Sequences by Nucleic Acid Hybridization

The quantity of nucleic acid present in a sample can be determined in several ways by nucleic acid hybridization, using methods well known to the art. The two methods are disclosed hereinafter using the example of quantitating R-RNA.

It will be understood that the present method is generally applicable in any case where it is necessary to determine the presence or absence of organisms which contain RNA or DNA and that such includes biological samples such as sputum, serum, tissue swabs, and other animal fluids and tissues as well as industrial and pharmaceutical samples and water. Specific details of the approach will change depending on whether RNA or DNA is being quantitated but the general approach is the same for both DNA and RNA.

TABLE 1

EXCESS SELECTED PROBE METHOD
PROBE: The probe is a specific, selected, marked sequence from a member of bacteria group B, which represents 10 percent of the base sequence of the R-RNA, and hybridizes completely with R-RNA from group B bacteria, but does not hybridize with R-RNA from other organisms. The probe cannot hybridize with itself.

| | | |
|---|---|---|
| A. Positive Homologous Control 0.1 microgram Probe + $10^{-3}$ micrograms Sample group B R-RNA | Hybridize to completion and assay strand probe | a) One percent of the probe will form double strand molecules. b) This is a direct measure of the R-RNA sample. The number of probe molecules hybridized equals the number of R-RNA molecules present. |
| B. Heterologous Control 0.1 micrograms Probe + $10^{-3}$ micrograms Sample human R-RNA | Hybridize to completion and assay for double strand probe | The probe does not hybridize with any R-RNA but R-RNA from group B bacteria |
| C. Unknown Sample 0.1 micrograms Probe + Unknown Sample | Hybridize to completion and assay for double strand probe | a) If no group B R-RNA is present, no probe will hybridize. b) If group B R-RNA is present, the probe will hybridize and form double strand molecules. c) The number of probe molecules hybridized equals the number of group B R-RNA molecules present. in the sample. d) If one percent of the probe hybridizes, group B R-RNA is present since the probe was selected so that it would hybridize only with R-RNA from a group B bacteria. Since |

TABLE 1-continued

EXCESS SELECTED PROBE METHOD
PROBE: The probe is a specific, selected, marked sequence from a member of bacteria group B, which represents 10 percent of the base sequence of the R-RNA, and hybridizes completely with R-RNA from group B bacteria, but does not hybridize with R-RNA from other organisms. The probe cannot hybridize with itself.

the probe will only hybridize to group B R-RNA, the presence of other R-RNAs will not interfere with the detection or the quantitation of any bacterial R-RNA present.
e) Using a selected probe makes it easier to ensure that the hybridization is complete. A selected probe representing 10 percent of the R-RNA sequence will hybridize 10 times faster than a probe which is representative of the total R-RNA sequence.
f) The detection of R-RNA in general is not possible since the probe hybridizes only with group B R-RNA. The sensitivity of detection of group B R-RNA is extremely high.

D. Summary
The excess probe method needs just one assay point in order to detect and quantitate group B organisms.

TABLE 2

EXCESS R-RNA METHOD: THE USE OF A SELECTED PROBE
PROBE: The probe is specific, selected, marked sequence from group B bacteria, which represents one-tenth of the R-RNA base sequence of one member of group B. The probe hybridizes completely with R-RNA from group B, but does not hybridize to R-RNA from other organisms. The probe cannot hybridize with itself.

| | | |
|---|---|---|
| A. Positive Homologous Control Sample 0.1 micrograms Group B R-RNA + $10^{-3}$ micrograms Probe | Hybridize to completion and assay for double strand probe | a) The fraction of probe which hybridizes is a direct measure of the similarity between the R-RNA and the probe. In this case 100 percent of the probe can hybridize. b) This percentage is not a |

TABLE 2-continued

EXCESS R-RNA METHOD: THE USE OF A SELECTED PROBE
PROBE: The probe is specific, selected, marked
sequence from group B bacteria, which
represents one-tenth of the R-RNA base
sequence of one member of group B. The
probe hybridizes completely with R-RNA
from group B, but does not hybridize to
R-RNA from other organisms. The probe
cannot hybridize with itself.

| | | |
|---|---|---|
| B. Heterologous Control Sample 0.1 micrograms human R-RNA + Probe 10⁻³ micrograms | Hybridize to completion and assay for double strand probe. | measure of the amount of R-RNA present. In order to determine this the kinetics of must be determined. The probe does not hybridize to non-bacterial R-RNAs. |
| C. Unknown Sample Sample + Probe 10⁻³ micrograms | Hybridize to completion and assay for double strand probe. | a) If no group B R-RNA is present in the sample there will be no hybridized probe. b) If group B R-RNA is present the probe will be hybridized. c) The amount of R-RNA can't be determined from the percentage hybridization at the completion of the reaction. In order to determine this the kinetics of the hybridization must be determined. Since the probe will hybridize with only one type of R-RNA, the kinetic determination is simple. d) If 100 percent of the probe has hybridized with the sample, this means that group B R-RNA is present in the sample. It does not indicate that only this R-RNA is present. Other R-RNAs which do not hybridize with the probe may also be present in the sample. e). If 100 percent of the probe hybridizes with the sample, it is possible to specifically quantitate the group B R-RNA in the present of human R-RNA by determining the kinetics of hybridization of the probe with the sample R-RNA. Since the probe will hybridize only with group B R-RNA such a kinetic reaction will have only one component, the one from reacting with group B R-RNA. f) There are situations where the hybridization can't go to completion. In this method the sample R-RNA must drive the hybridization to completion, since only a very small amount of probe is present. If there is not sufficient R-RNA in the sample, the hybridization will not be completed. The interpretation of such a situation is discussed below If hybridization of unknown sample results in 20 percent hybridization of the probe at the usual assay time, it is not possible to tell if the reaction is complete with only one time-point. It is necessary to take another point at double the original time to determine if the hybridization value increases. If it does not increase then the hybridization is complete. In this case the R-RNA is at such low concentration in the sample that the probe is in excess and the number of R-RNA molecules present in the sample is equal to the number of probe molecules hybridized. If the hybridization value is increased, the hybridization was not over at the first time-point. A third time-point must then be done to determine whether the reaction was over at the second time point. |

D. Summary
The excess sample R-RNA method needs multiple assay points in order to detect and quantitate, and is much more time-consuming that the excess probe method.

Use of Selected Probes Complementary to only a Particular Fraction of the R-RNA Sequence from a Particular Source to Detect R-RNA Versus use of Unselected Probes Complementary to the Entire R-RNA Sequence from a Particular Source to Detect R-RNA One aspect of my invention, which comprises using specifically selected probes complementary to only a particular fraction of the R-RNA sequences to detect, quantitate, and identify R-RNA has important capabilities and advantages over another aspect of the invention, that of using unselected probes or sequences complementary to the entire R-RNA sequence to detect R-RNA. The advantages of using a selected probe in both excess R-RNA and excess probe hybridization methodologies are set forth below. The problems with using a completely representative probe are also presented.

The advantages of using a selected probe over using a completely representative R-RNA probe, with excess probe hybridization, as well as with excess R-RNA hybridization, is set out below:

| Advantages of the Excess Probe Hybridization Method | |
|---|---|
| Problems with Completely Representative R-RNA Probe | Advantages of Using Selected Probes |
| 1. R-RNA can be detected in a sample with the excess probe method but there is no way of determining the type of R-RNA present. Thus this probe can't be used to specifically detect and quantitate the presence of a particular R-RNA in an unknown sample, with the excess probe hybridized method. | The selected probe can be used to sensitively and specifically detect and quantitate the presence of a particular R-RNA, in an unknown sample when used in an excess probe hybridization method. This can be done with just one lab assay, even in the presence of R-RNA from other organisms. |
| 2. As stated above, the excess probe method cannot be used with this probe to detect or quantitate the presence of a particular R-RNA in a sample. For this purpose the probe must be used in the excess R-RNA method. The excess R-RNA method is much more time consuming, requires much more work, and is much more complicated than the excess probe method. | The use of a selected probe makes it possible to use the excess probe method for detecting and quantitating the presence of a particular R-RNA in an unknown sample. This greatly simplifies the task. |

| Advantages of the Excess R-RNA Hybridization Method | |
|---|---|
| Problems with Completely Representative Probe | Advantages of Using Selected Probe |
| 1. R-RNA can be detected in an unknown sample with this probe, but in many cases there is no way of determining the type or quantity of R-RNA which is present. Thus in many instances the probe cannot be used to specifically detect and quantitate the presence of a particular R-RNA in an unknown sample. | The selected probe can be used to specifically detect and quantitate the presence of a particular R-RNA in an unknown sample in all situations. This can be done even in the presence of large amounts of R-RNA from other organisms. |
| 2. In many cases the sensitivity of detection of a specific R-RNA is limited by the presence of R-RNA from other organisms. | With the selected probe the presence of R-RNA from other organisms does not lower the sensitivity of detection of a particular R-RNA. |
| 3. In many cases where it is possible to detect and quantitate the presence of particular R-RNA, it requires a lot of, work. | The detection and quantitation of the presence of a particular R-RNA is much easier then a selected probe is utilized. |

Illustrative Embodiments

My invention, illustratively, may be used to determine whether a sample contains any member of a particular group of living organisms. The method, described in the following examples, is a test which may be used to detect and quantiate the presence of any member or members of a particular group of bacteria in a sample, even in the presence of large numbers of organisms which are not members of that particular group.

As set forth in the examples, applicant's method involves first producing a group specific R-RNA probe which, at a specific criterion, hybridizes to R-RNA from any member of the specific group of interest, but does not hybridize to R-RNA from any other organisms. The use of such a probe in a nucleic acid hybridization test allows the detection of any member of that specific group, even in the presence of large numbers of other organisms.

Examples of the practice of the invention are listed later. Each example involves the production of a marked nucleic acid probe which will hybridize only with R-RNA from members of a particular group of organisms.

The basic outline of the method used to produce each probe is as follows:

1. Produce marked nucleic acid complementary to the R-RNA of a member of the group of interest.
2. Hybridize this DNA to R-RNA from a member of the group or groups of organisms evolutionarily most closely related to the group of organisms for which the probe is to be specific. Select the fraction of the marked nucleic acid which, at a specific criterion, does not hybridize to R-RNA from a member of this closest related group of organisms. This fraction is specific for the R-RNA of the organisms group of interest and does not hybridize with R-RNA from the most closely related group or groups or any other organism.

EXAMPLE 1

Production of Probe which will Hybridize to R-RNA from any Bacteria

In a typical situation, about $10^6$ to $-10^7$ mammalian cells are grown in a tissue culture plate at one time. Bacterial species, especially members of the taxonomic Class Mollicutes, are known to contaminate tissue culture cells. Members of the Class Mollicutes, unlike most other bactera, are not readily eliminated by antibiotics, and are troublesome contaminants of cell cultures. Many different Mollicutes species have been detected in tissue culture cells. If just one of these organisms is present in the culture plate, it has the potential, even in the presence of antibiotics, to multiply and produce hundreds of organisms per cell. Such organisms are capable of altering the activity of cells, thereby affecting the results of various studies and the marketability of cell culture products.

Prior art methods for detecting these organisms involve basically qualitative tests, the most commonly used being growth tests, differential staining tests and immunologic assays. The growth tests, while quite sensitive, take 3–6 weeks. They have the additional disadvantage that many organisms are difficult or impossible to grow.

While the actual detection sensitivity of the staining method is not known, it is known that more than several organisms per cell have to be present.

Immunologic tests are qualitative tests and involve using antibody toward a particular species. While they can be carried out rapidly, they are not very sensitive; furthermore, many different antibodies would be required to detect all types of Mollicutes.

The embodiment of applicant's method described below, is a test which may be used to detect and quantitate the presence of any member of the group of all bacteria, including the taxonomic Class Mollicutes, to detect the presence of Mollicutes in tissue culture, to detect the presence of bacteria in the tissue which is normally free of bacteria, and to detect the presence of the bacteria even in the presence of large numbers of mammalian cells.

As set forth in the example, applicant's method involves first making a specific R-RNA probe which is complementary to R-RNA from any bacteria but is not complementary to mammalian cell R-RNA. The use of such a probe in a nucleic acid hybridization test allows the detection of any bacterial type, even in the presence of large numbers of mammalian cells.

A detailed description of this embodiment of the invention follows:

Preparation of R-RNA from Mammalian and Bacterial Cells

Mammalian cells are resuspended in a 0.3M Nacl, 0.02M Tris, pH=7.4. Sarkosyl is added to a final concentration of 1 percent to lyse the cells. Immediately upon lysis an equal volume of a 1/1 mixture of phenol/chloroform is added and the resulting mixture shaken vigorously for 2 minutes. The mixture is then centrifuged (8000×g for 10 minutes) to separate the aqueous and organic phases. The aqueous phase is recovered, and to this is added another volume of phenol/chloroform. After shaking and centrifugation as above, the aqueous phase is again recovered. To this is added 2 volumes of 95% ethanol and this mixture is placed at −20° C. for 2 hours to facilitate precipitation of the nucleic acids. Then the mixture is centrifuged (8000×g, 10 minutes) in order to sediment the precipitate to the bottom of the tube. The liquid is then removed. The pelleted nucleic acid is redissolved in water. This solution is then made to 0.2 m NaCl, $5 \times 10^{-3}$ m $MgCl_2$, $5 \times 10^{-3}$M $CaCl_2$, 0.02M Tris (pH=7.4), 50 micrograms per ml of deoxyribonuclease I and incubated at 37° C. for 1 hour. Then add an equal volume of phenol/chloroform and shake as above. Centrifuge as above and recover the aqueous phase. Ethanol precipitate the RNA as above. Centrifuge the precipitate as above and redissolve the pelleted RNA in water. Make this solution to 2M LiCl and place it at 4° C. for 10–20 hours in order to facilitate the precipitation of the high molecular weight RNA. Then centrifuge this solution to collect the precipitate and redissolve the precipitate in water. This preparation of RNA contains greater than 95% R-RNA.

Bacterial R-RNA is isolated in a similar manner with the following exceptions. In those cases where detergent alone does not lyse the bacteria, other means are employed. This usually involves pretreating the bacteria with an enzyme (lysozyme) to make then susceptible to lysis by sarkosyl. After lysis of the bacteria the isolation procedure is as described above.

Purified R-RNA is stored at −70° C.

Production of Radioactive DNA Complementary ($^3$H-cDNA) to Mollicutes R-RNA

R-RNA from the species *Mycoplasma hominis* (*M. hominis*), a member of the taxonomic class Mollicutes, is used as a template to synthesize radioactive cDNA complementary to *M. hominis* R-RNA.

This cDNA is produced by utilizing the ability of an enzyme, reverse transcriptase, to utilize R-RNA as a template and produce $^3$H-cDNA complementary (cDNA) to R-RNA. The reverse transcriptase reaction mixture contains the following: 50 mM Tris.HCL (pH=8.3), 8 mM $MgCl_2$, 0.4 mM dithiothreitol, 50 mM KCL, 0.1 mM $^3$H-deoxythymidinetriphosphate (50 curies per millimole), 0.2 mM deoxyadenosinetriphosphate, 0.2 mM deoxycytidinetriphosphate, 0.2 mM deoxyguanosinetriphosphate, 200 micrograms per ml of oligodeoxyribonucleotide primer made from *E. coli* DNA, 50 micrograms per ml of *M. hominis* R-RNA and 50 units per ml of AMV reverse transcriptase. This mixture is incubated at 40° C. for 30 minutes. Then ethylene diamine tetraacetic acid (EDTA) (pH=7.3), sodium dodecyl sulfate (SDS), NaCl and glycogen are added to final concentrations of $10^{-2}$M, 1 percent, 0.3M, and 100 micrograms per ml respectively. The solution is then mixed with 1 volume of phenol/chloroform (1/1) and shaken vigorously for 2 minutes, then centrifuged (8000×g for 10 minutes) and the aqueous phase recovered. The nucleic acids are precipitated by the addition of 2.5 volumes of 95% ethanol. The precipitate is recovered by centrifugation and redissolved in $H_2O$. This solution contains the template R-RNA and the newly synthesized $^3$H-cDNA.

This solution is then, make to 0.3M NaOH and incubated at 50° C. for 45 minutes, and cooled in ice and neutralized with 0.3M HCl. Two and one-half volumes of 95% EtOH are then added to precipitate the remaining nucleic acid and the resulting precipitate redissolved in water. This solution is then passed over a Sephadex G-100 column equilibrated to 0.3M NaCl, 0.1 percent sarkosyl and the excluded volume recovered. This solution is ethanol precipitated and the resulting precipitate redissolved in a small volume of water. The process described in this paragraph removes the template R-RNA and any remaining precursor material from the $^3$H-cDNA preparation.

The $^3$H-cDNA is then hybridized to *M. hominis* R-RNA to ensure that it is indeed complementary to this R-RNA. The hybridization mixture consists of, 0.05 micrograms of single strand $^3$H-cDNA, 20 micrograms of *M. hominis* R-RNA, and 0.48M PB (phosphate buffer) in 1 ml. This mixture is incubated for 0.2 hours at 65° C. and is then diluted to 0.14M PB and passed over a hydroxyapatite (HA) column equilibrated to 0.14M PB and 65° C. $^3$H-cDNA hybridized to R-RNA absorbs to the hydroxyapatite (HA) column while non-hybridized $^3$H-cDNA passes through the column. The hybridized $^3$H-cDNA is then recovered by elution of the HA column with 0.3M PB. This fraction is then dialysed to remove the PB, ethanol precipitated to concentrate the nucleic acid, centrifuged and the nucleic acid redissolved in water. This solution is then treated with NaOH as described above in order to remove the R-RNA. After neutralization, addition of glycogen carrier and concentration by ethanol precipitation, the $^3$H-cDNA is redissolved in a small volume of water. This solution contains only $^3$H-cDNA which is complementary to *M. hominis* R-RNA.

Selection of $^3$H-cDNA which is Complementary to *M. hominis* RNA but is not Complementary to Human R-RNA The purified $^3$H-cDNA is further fractionated by hybridizing it with a great excess of human R-RNA. The hybridization mixture consists of 0.05 micrograms of H-cDNA, and 40 micrograms of human R-RNA in one ml of 0.48M PB. This is incubated at 68° C. for 1 hour and the mixture is then diluted to 0.14M PB and passed over HA equilibrated to 55° C. and 0.14M PB. The fraction (about 50% of the total) which does not adsorb to the HA (i.e., $^3$H-cDNA not hybridized to human R-RNA) is collected. This fraction is repassed over a new HA column under the same conditions. Again the non-adsorbed fraction is collected. This fraction is dialysed to remove the PB, ethanol precipitated to concentrate the nucleic acid and redissolved in water. This solution is treated with NaOH, as described earlier, in order to remove the human R-RNA. After neutralization, addition of glycogen carrier, and concentration by ethanol precipitation, the $^3$H-cDNA is redissolved in a small volume of water. This $^3$H-cDNA preparation is complementary to *M. hominis* R-RNA but is not complementary to human R-RNA.

Hybridization of Selected ⁴H-cDNA with R-RNA from Different Source

The production of the selected ³H-cDNA probe allows the detection of bacteria, including members of the Class Mollicutes in mammalian tissue culture cells and mammalian tissues by detecting the presence of bacterial R-RNA by nucleic acid hybridization. A necessary requirement of such a test is that the selected probe must not hybridize to R-RNA from mammalian cells which do not contain bacteria. That this requirement is met is shown in Table 3V.

Table 3, parts II and III shown that the probe will detect all members of the class Mollicutes and should detect all types of bacteria. For example, *Legionella p.* and *E. coli* and *Bacillus subtilis* are representative of very different bacterial types and the probe hybridizes with R-RNA from each of these types. Evolutionary considerations indicate that this probe will hybridize to R-RNA from virtually any known or unknown bacteria. This is due to the extreme conservation of the R-RNA nucleotide sequence during evolution.

This selected probe is useful for detecting the presence of a specific Class of bacteria, Mollicutes, in tissue culture cells. In most tissue culture cells antibiotics are present in the growth medium and this prevents the growth of virtually all bacteria but members of the Class Mollicutes. Thus any contamination of a tissue culture preparation is almost certain to be due to a member of the Class Mollicutes.

An imporatnad aspect is the ability to determine the number of organisms present. In most cases, cell lines and their products are discarded when cells are shown, by prior art methods, to be contaminated. The ability to quantitate these organisms makes it possible to make judgements as to the severity of any effects due to contamination. The degree of a contamination may be very light, and only one organism per 1000 cells present. This level of contamination would have very little effect on the cells and in many situations the cell products need not be discarded. The decision might be made to retain valuable cell lines until they become more heavily contaminated. Quantitative considerations are important for judging the importance of any kind of a bacterial contamination.

TABLE 3

Hybridization of Selected Mollicutes ³H-cDNA with R-RNA from Widely Different Sources

| | Source of R-RNA | Percent Hybridization of H-cDNA with R-RNA |
|---|---|---|
| I. Control Experiments | A. No R-RNA added, Self Reaction of ³H-cDNA | <1% |
| | B. Mock R-RNA isolation | <1% |
| | C. Human cell RNA known to be contaminated with *M. hominis* R-RNA | 97% |
| II. Hybridization of ³H-cDNA with R-RNA from different species of taxonomic Class Mollicutes | A. Members of the Order of Mycoplasmatales | |
| | 1. *Mycoplasma hominis* (infects humans) | 97% |
| | 2. *Mycoplasma salivarius* (infects humans) | 93% |
| | 3. *Mycoplasma hyorhinis* (infects pigs) | 84% |
| | 4. *Mycolpasma pulmonis* (infects mice) | 82% |
| | B. Members of the Order Acholeplasmatacese | |
| | 1. *Acholeplasma laidlawii* isolate #1 | 52% |

TABLE 3-continued

Hybridization of Selected Mollicutes ³H-cDNA with R-RNA from Widely Different Sources

| | Source of R-RNA | Percent Hybridization of H-cDNA with R-RNA |
|---|---|---|
| | (infects cows, birds, dogs, house cats, mice, sheep, pigs, and primates) | |
| | 2. *Acholeplasma laidlawii* (isolate #2) | 53% |
| | C. Members of the Order Spiroplasma taceae | |
| | 1. SMCA (infects insects and mice) | 69% |
| | 2. Honey bee (isolated from honey bee) | 68% |
| | 3. Cactus (isolated from cactus) | 71% |
| | 4. Corn Stunt (isolated from corn) | 69% |
| | 5. Corn Stunt (isolated from insect) | 65% |
| III. Hybridization of ³H-cDNA with R-RNA from other types of bacteria (taxonomic Class Schizomytes) | A. Member of the Family *Enterobacteraceae* | |
| | 1. *Escherischia coli* (infects mammals) | 52% |
| | B. Member of the Family *Legionellaceae* | |
| | 1. *Legionella pneumophila* (infects man) | >28% |
| | C. Member of the Family *Micrococcaceae* | |
| | 1. *Micrococcus luteus* | 50–60% |
| | 2. *Staphylococcus aureus* | 50% |
| | D. Member of the Family *Lactobacillaceae* | |
| | 1. *Streptococcus faecalis* | |
| | E. Member of the Family *Bacillaceae* | 40% |
| | 1. *Bacillus subtilis* | |
| IV. hybridization of ³H-cDNA with R-RNA Yeast | | 2% |
| V. Hybridization of ³H-cDNA with R-RNA from mammals and a bird | Human (primate) | 1% |
| | Cow (bovine) | 1% |
| | Mouse (rodent) | 1% |
| | Rat (rodent) | 1% |
| | Hamster (rodent) | 1% |
| | Rabbit (lagomorph) | 1% |
| | Chicken (avian) | 1% |

Excess R-RNA hybridizations are done at 68° C., 0.48M PB. Hybridization assays are done with hydroxyapatite at 67° C. in 0.14M PB, 0.005% sodium dodecyl sulfate. The hybridization exposure is sufficient to ensure complete reaction of the ³H-cDNA with nuclear R-RNA or for mitochondrial R-RNA. Non-bacterial R-RNA Cot's of at least 2×10³ are reached in the case of the mammals and bird. A non-specific signal of 1–2 percent has been substracted from the hybridization values presented above.

Quantitation of R-RNA by Nucleic Acid Hybridization

The amount of bacterial R-RNA present in a sample can be determined by measuring the kinetics of hybridization of the selected $^3$H-c-DNA probe with the RNA isolated from a tissue and comparing these kinetics to those of a known standard mixture. This can be done even in the presence of a large excess of mammalian cell R-RNA since the probe does not hybridize with this R-RNA (see Table 3, V).

For measuring the kinetics, the hybridization mixtures contain, $10^{-5}$ to $10^{-4}$ micrograms of $^3$H-cDNA and 1 to $10^3$ micrograms of purified sample RNA in 0.01 to 0.1 ml of 0.48M PB. This mixture is incubated at 68° C. and aliquots are removed, diluted to 0.14M PB and assayed for hybridization at various times after the initiation of the reaction. Hybridization assays are performed using hydroxyapatite as described earlier. The results obtained are compared to the hybridization of the probe reacted with standard RNAs containing known amounts of bacterial R-RNA. These standards are mixtures of mammalian cell RNA and known amounts of a specific bacterial R-RNA.

Detection and Quantitation of Members of the Class Mollicutes in Tissue Culture Cells Table 4 presents data obtained by hybridizing the selected probe with RNA isolated (as described earlier) from three different tissue culture cell sampels. Only cell line number 3 is detectably contaminated and the kinetics of the reaction indicated that about $5 \times 10^7$ bacterial cells are present in the tissue culture cells.

TABLE 4

Detection and Quantitation of Mollicutes in Tissue Culture Cells

| Cell Line | Hybridization Time (hours) | Percent Hybridization of $^3$H-cDNA with RNA | Number of Bacteria Detected |
|---|---|---|---|
| 1. 44-2C (rat) | 17 | 1 | None detected |
|  | 40 | 1 | None detected |
| 2. P388 D1M (mouse) | 1.1 | 1 | None detected |
|  | 22.5 | 1 | None detected |
| 3. P388 D1C (mouse) | 0.025 | 20 | $5 \times 10^7$ |
|  | 16.2 | 78 | (about 1 Mollicute per cell) |

Excess R-RNA Hybridizations are done at 68° C. in 0.48M PB in a volume of 0.01 to 0.04 ml. Each mixture contains $2 \times 10^5$ micrograms of $^3$H-cDNA probe and 50–200 micrograms of sample RNA.

The following example is another embodiment of the method of my invention, used for detecting very small numbers, even one trypanosome, in the presence of a large number of blood cells.

The detection of trypanosomes is important since certain members of the protozoan group Trypanosoma are pathogenic for humans, causing diseases that include East African sleeping sickness, West African sleeping sickness, and South American trypanosomiasis. These organisms are large and have varying characteristic shapes, depending on the stage of the life cycle. Prior art methods rely mainly on serologic, differential staining coupled within microscopic examination and animal inoculation procedures for detecting these organisms in humans. The serodiagnostic methods vary in sensitivity and specificity and may be difficult to interpret. The microscopic methods are most used, however small numbers of the trypanosomes are often difficult to detect in the presence of large numbers of blood cells. Animal inoculation is a long and costly procedure.

The embodiment of the invention set forth in the following example is a method which makes it relatively easy to detect the presence of one trypanosome even when co-present with a large number of blood cells.

EXAMPLE 2

Production of Radioactive DNA Complementary to Trypanosome R-RNA

Radioactive DNA complementary ($^3$H-cDNA0 to *trypanosoma brucei* R-RNA is produced in the same way as *M. hominis* $^3$H-cDNA, which is described above in detail, except that *Trypanosoma b*. R-RNA is used as a template.

Selection of Trypanosome $^3$H-cDNA which is Complementary to Trypanosome R-RNA but is not Complementary to Human R-RNA This is done in the same way as described earlier for *M. hominis* except that *Trypanosoma b*. $^3$H-cDNA is hybridized to the human R-RNA.

Use of Selected Trypanosome $^3$H-cDNA to Detect and Quantitate Trypanosomes in Human Tissue or Fluid The production of the selected $^3$H-cDNA probe allows the detection and quantitation of trypanosomes in human samples by detecting the presence of trypanosome R-RNA. A necessary requirement of such a test is that the selected probe must not hybridize to R-RNA from human cells which do not contain trypanosomes. Table 5 shown that this requirement is met.

TABLE 5

Hybridization of Selected *Trypanosoma brucei* $^3$H-cDNA with R-RNA from Different Sources

| R-RNA Source | Percent Hybridization of $^3$H-cDNA with R-RNA |
|---|---|
| No RNA added | 1% |
| *Trypanosome brucei* R-RNA | 98% |
| Bacterial (Mycoplasma hominis) R-RNA | 1% |
| Human R-RNA | 1% |
| Human R-RNA known to be contaminated with *Trypanosome brucei* | 98% |

Excess R-RNA hybridizations are done at 65° C. in 0.48M PB. Reactions are run for 24 hours and the hybridization exposure is sufficient to ensure complete reaction of the human nuclear or mitochondrial R-RNAs and the baterial R-RNA. Hybridization assays are done with hydroxyapatite at 72° C. in 0.14M PB, 0.005% sodium dodecyl sulfate.

One illustrative probe which I have prepared is specific only for members of the Genus Legionella. The probe hybridizes to greater than fifth percent with nucleic acids from diverse members of the Genus Legionella, and does not hybridize significantly with nucleic acids from mammals, yeast and a variety of widely diverse bacterial strains (Table 8). The probe hybridizes well even with Legionella species such as *L. pneumophila* and *L. micdadei* which show little or not bulk DNA relatedness. Other known Legionella species can be detected by this probe used in Table 6; as listed in Table 7. All of the known Legionella species (thus far 23 different species) have been examined and all can be specifically detected with the probe used in Table 6.

The specificity of this probe makes it possible to detect and quantitate the presence of Legionella species, even in the presence of large numbers of non-related bacterial or mammalian cells. Thus, liver cells from a *L. pneumophila* infected hamster was assayed for the presence and number of Legionella organisms by using the specific probe and well established nucleic acid hybridization procedures. The liver had previously been assayed by a microbiological growth test which indicated that about $10^7$ Legionella organisms per gram were present in the infected liver. Nucleic acid hybridization analysis indicated about $1-2\times10^8$ Legionella organisms per gram of liver. These results suggest that the plating efficiency in the growth test is about 5–10 percent.

The specific probe allows the highly sensitive and rapid detection of Legionella organisms even in the presence of large numbers of mammalian cells. In an assay which took less than 1 day the probe easily detected the presence of about 400 Legionella organisms which were mixed with 0.4 mg of liver (about $2\times10^5$ cells).

TABLE 6

Hybridization of Legionella Specific Probe With Nucleic Acids from Widely Different Sources

|  | Nucleic Acid Source | Normalized Percent Probe Hybridized |
|---|---|---|
| I. Controls | 1) No nucleic acid | 1 |
|  | 2) Mock nucleic acid Isolation | 1 |
|  | 3) L. pneum. infected hamster tissue | 100 (Actual percent = 81) |
| II. Legionella- | 1) L. bozemanii (WIGA) | >50 |
| ceae | 2) L. dumoffii (TEX-KL) | >50 |
|  | 3) L. garmanii (LS-13) | >50 |
|  | 4) L. jordanis (BL540) | >50 |
|  | 5) L. longbeachae | >50 |
|  | 6) L. micdadai (HEBA) | >50 |
|  | 7) L. MSH9 | >50 |
|  | 8) L. oakridgenis (Oakridge 10) | >50 |
|  | 9) L. pneumophila (PHA 1) | 100 |
|  | 10) L. Lansing 2 | 50 |
|  | 11) L. SC-32C-C8 | 50 |
| III. Other | 1) Aeormonas hydrophila | 1 |
| Bacterial | 2) B. subtilis | 1 |
| Species | 3) Camplyobacter jejuni | 1 |
|  | 4) Cytophaga johnsonae | 1 |
|  | 5) E. coli | 1 |
|  | 6) Flavobacterium breve | 1 |
|  | 7) Flavobacterium gleum | 1 |
|  | 8) Flavobacterium meningosepticum | 1 |
|  | 9) Flavobacterium multivarum | 1 |
|  | 10) Flavobacterium spiritovarum | 1 |
|  | 11) Flavobacterium thalophohilum | 1 |
|  | 12) Flexibacter canadensis | 1 |
|  | 13) Proteus mirabilis | 1 |
|  | 14) Proteus rettgeri | 1 |
|  | 15) Proteus vulgaris | 1 |
|  | 16) Providencia alicalifaciens | 1 |
|  | 17) Providencia stuartii | 1 |
|  | 18) Pseudomonas alcaligenes | 1 |
|  | 19) Vibrio El Tor | 1 |
|  | 20) Mycoplasma hominis |  |
|  | 21) Mycoplasma hyorphinis | 1 |
|  | 22) Mycoplasma salivarium | 1 |
|  | 23) Acholeplasma Laidlawii | 1 |
|  | 24) Spiroplasma SMCA | 1 |
|  | 25) Spiroplasma corn stunt | 1 |
|  | 26) Spiroplasma honey bee | 1 |
|  | 27) Spiroplasma cactus | 1 |
| IV. Yeast | S. cerv | 1 |
| V. Mammals | Human | 1 |
|  | Hamster | 1 |
|  | Mouse | 1 |

Excess R-RNA hybridizations are done at 76° C., 0.48M PB. Hybridization assays are done with hydroxyapatite at 72° C. in 0.14M PB, 0.005% sodium dodecyl sulfate. The hybridization exposure is sufficient to ensure complete reaction of the $^3$H-cDNA with nuclear R-RNA or for mitochondrial R-RNA. Non-bacterial R-RNA Cot's of at least $2\times10^3$ are reached in the case of the mammals and birds.

TABLE 7

Other Legionella Species Which Can Be Detected By Specific Nucleic Acid Probe of Table 7

Species

L. WA-316
L. WO-44-3C (L. feeleii)
L. Phoenix-1
L. WA-270 A
L. PF-209C-C$_2$
L. SC 65C3 (ORW)
L. Jamestown 26G1-E2
L. MSH-4
L. Lansing 3
L. SC-18-C9
L. SC-63-C7
L. 81-716 (L. wadsworthii)

EXAMPLE 3

Production of a Probe which will Hybridize only to R-RNA from Members of the Genus Legionella Production of Radioactive DNA Complementary to Legionella R-RNA R-RNA from the species Legionella pneumophila is used as a template to synthesize marked (radioactive) cDNA (complementary DNA) complementary to Legionella pneumophila R-RNA. This cDNA is produced by utilizing the ability of an enzyme, reverse transciptase, to utilize R-RNA as a template and produce $^3$H-cDNA complementary to R-RNA. This is done in the same way as described for producing M. hominis $^3$H-cDNA except that R-RNA from Legionella pneumophila is used as a template.

Selection of Radioactive Probe which Hybridizes only to R-RNA from Members of the Genus Legionella The purified $^3$H-cDNA is fractionated by hybridizing it with a great excess of R-RNA from E. coli, Acheolaplasma laidlawaii and Providentia stuartii. The hybridization mixture consists of 0.65–1 micrograms of $^3$H-cDNA and 20 micrograms of each bacterial R-RNA in 1 ml of 0.48M PB. This mixture is incubated at 76° C. for 1 hour and the mixture is then diluted to 0.14M PB and passed over HA equilibrated to 72° C., 0.14M PB. The fraction of $^3$H-cDNA which does not absorb to the HA (i.e., the $^3$H-cDNA not hybridized to the R-RNA) is collected. This fraction is then passed over HA under the same conditions as above and again the non-adsorbed fraction is collected. This $^3$H-cDNA is then concentrated and again hybridized with bacterial R-RNA as described above. The non-adsorbed fraction is collected and concentrated and then hybridized with bacterial R-RNA for a third time as described above and fractionated on HA as above. The non-adsorbed fraction is collected, base treated to remove any R-RNA present and concentrated into water. This $^3$H-cDNA preparation will hybridize to any member of the Legionella genus and will not hybridize to R-RNAs from other sources.

Hybridization of Legionella specific $^3$H-cDNA Probe with R-RNA and R-RNA Genes from Different Sources The selected probe allows the detection of any member of the genus Legionella in a sample by detecting the presence of Legionella R-RNA by nucleic acid hybridization. A necessary requirement of such a test is that the Legionella specific probe must not hybridize to R-RNA from other sources.

Quantitation of Legionella R-RNA by Nucleic Acid Hybridization Excess R-RNA Method:

The amount of baterial R-RNA present in a sample can be determined by measuring the kinetics of hybridization of the selected $^3$H-cDNA probe with the RNA isolated from a tissue sample and comparing these kinetics to those of a known standard mixture. This can be done even in the presence of a large excess of mammalian cell R-RNA since the probe does not hybridize with this R-RNA.

For measuring the kinetics, the hybridization mixture may contain, for example, $10^{-5}$ to $10^{-4}$ micrograms of $^3$H-cDNA and 0.01 to $10^3$ micrograms of purified sample RNA in 0.01 to 0.1 ml of 0.48M PB. This mixture is incubated at 76° C. and aliquots are removed, diluted to 0.14M PB and assayed for hybridization at various times after the initiation of the reaction. Hybridization assays are performed using hydroxyapatite as described earlier. The results obtained are compared to the hybridization kinetics of the probe reacted with standard RNAs containing known amounts of bacterial R-RNA. These standards are mixtures of mammalian cell RNA and known amounts of a specific bacterial R-RNA.

Table 8 presents data on the quantitation of *Legionella pneumophila* present in water samples and in an infected hamster liver sample. The water samples and the liver samples were titered for the presence of *L. pneum* by standard quantitative growth assays at the Center for Disease Control in Atlanta, Ga.

TABLE 8

| | Measured by a Growth Assay | Measured by Excess R-RNA Nucleic Acid Hybridization |
|---|---|---|
| *L. pneumophila* bacteria per gram of infected hamster liver | $10^7$ bacteria gram liver | $1 - 2 \times 10^8$ bacteria gram liver |
| *L. pneumophila* bacteria per ml of water sample Excess. Probe Method | $1.5 \times 10^8$ bacteria ml | $2.1 \times 10^8$ bacteria ml |

The amount of bacterial R-RNA present in a sample can also be measured by doing hybridization under conditions where there is an excess of the Legionella specific $^3$H-cDNA probe, relative to the amount of Legionella R-RNA present. This mixture is hybridized to completion. At this point each Legionella R-RNA molecule present in the sample is saturated with probe molecules. By comparing the amount of probe hybridized to the R-RNA to an appropriately constructed standard calibration curve, the amount of R-RNA in a sample can be determined. A good estimate of the total number of *Legionella pneumophila* bacteria present in the sample can then be calculated by knowing the average number of R-RNA molecules per *L. pheumophila* bacterium.

Table 9 presents data on the quantitation of *L. pneumophila* present in water samples as determined by the excess probe accelerated hybridization rate—enzyme-detergent-sample method described in detail in a later section. The water samples were titered for the presence of *L. pneumophila* by standard quantitative growth assays. These assays take days to complete while the hybridization assay takes about 1 hour.

TABLE 9

| | Measured by Growth Assay | Measured by the Excess Probe Method |
|---|---|---|
| *L. pneumophila* bacterial per ml water sample | $1.5 \times 10^8$ bacteria ml | $2.2 \times 10^8$ bacteria ml |

Probe Specific Only for R-RNA from Members of the Genus Legionella

A. Analysis of a Water Sample: Accelerated Hybridization Rate Method

1. Preparation of Sample and Hybridization Incubation Mixture:

Mix in the following order as quickly as possible.

a) 9 microliters of sample b) 2 microliters of enzyme-detergent solution containing:
  5 milligrams/ml Proteinase K, 0.5M Tris (pH=8.1), 8% sodium dodecyl sulfate (SDS), 4% sodium sacrosinate, 0.25M NaCl, 0.016M EDTA, 0.016 EGTA c) 1 microliter of probe dissolved in water d) 20 microliters of 4.8M PB 2. Incubate the mixture at 76° for an appropriate time so that the hybridization reaction is complete.

3. The hybridization assay is performed as follows:

a) Add the incubation mixture to one ml of a room temperature solution containing: 0.05 grams hydroxyapatite (HA), 0.054M PB, 0.02% Zwittergent 14 (CalBiochem) (hereinafter referred to as Z-14)

b) Shake the mixture for 30 seconds at room temperature, add 5 ml 0.14M PB, 0.02% Z-14, and incubate the mixture at 72° C. for 2 minutes.

c) Centrifuge the solution to pellet the HA. All centrifugations are done at room temperature. Decant and save the liquid fraction. This is wash #1.

d) Add 6 ml of 0.14M PB, 0.02% Z-14 solution to the pellet. Resuspend the HA pellet by vortexing it. Centrifuge to pellet the HA and decant and save the liquid fraction. This is wash #2.

e) Repeat step d. This results in wash #3.

f) Add 6 ml 0.03 and resuspend the HA pellet by vortexing. Centrifuge the suspension to pellet the HA and decant the liquid and assay it for the presence of the probe. This fraction contains the hybridized probe, if any is present.

It is not necessary to elute the hybridized probe from the HA under certain conditions. Thus, if the probe is marked with a marker which can be detected in the presence of HA, the pellet from step e can be assayed directly for the probe. In the case of a marker such as a Iodine-125 the tube containing the HA pellet can be placed directly into a gamma detection machine.

Other modifications can also be made to make the test faster and easier. Thus, the volume and amount of HA used can be scaled down, and the number of washes can also be reduced, depending on the situation. In other instances it may be desirable to increase the volumes of HA or number of washes. A variety of salts other than sodium phosphate, and other detergents can also be used in the array.

Analysis of a Liquid Sample: Standard Hybridization Rate Method

1. Preparation of Sample and Hybridization Incubation mix.

Mix in the following order and as quickly as possible.

a) 14 microliters of sample b) 2 microliters of enzyme-detergent solution described in A.

c) 1 microliter of probe d) 3 microliters of 3.2M PB, 0.03M EDTA, 0.03M EGTA

2. Incubate the mixture at 76° C. for an appropriate time so that hybridization will complete.

3. The hybridization assay is performed as follows:

a) Add the incubation mix to 1 ml of a solution containing 0.14M PB, 0.02%, Z-14, 0.05 grams of HA.

b) From this point on the protocol is identical to that described in A.

C. Analysis of Tissue Sample: Accelerated Hybridization Rate Method

A 10 percent liver homogenate in water is used as the tissue sample.

1. Preparation of Sample and Incubation Mix.

Mix as quickly as possible in the following order.

a) 8 microliters of sample (10% liver homogenate)

b) 3 milliliters of enzyme-detergent mix containing: 8% SDS, 4% sodium sarcosinate, 0.25M NaCl, 0.016M EDTA, 0.016M EGTA, 0.38M Tris (pH=8.2), 195 milligrams/ml of Pronase.

c) 1 microliter of probe specific only for Legionella R-RNA.

d) 20 microliters of 4.8M PB.

2. Incubate the mixture at 76° for an appropriate time to ensure that the hybridization reaction is complete.
3. The hybridization assay is performed as described in the section on analysis of a water sample: Accelerated Rate Method.

D. Analysis of Tissue Sample: Standard Hybridization Rate Method

A 10 percent liver homogenate in water, used as the sample.

1. Preparation of the Sample and Incubation Mix.

Mix as quickly as possible in the following order.

a) 12 microliters of sample.

b) 4 microliters of enzyme-detergent solution described in B.

c) 1 microliter of probe specific only for Legionella R-RNA.

d) 3 microliters of 3.2M PB, 0.03M PB, 0.03M EGTA.

2. Incubate the mix for an appropriate time at 76° C.
3. The hybridization assay is performed as follows.

a) add the incubation mix to 1 ml of a solution containing 0.14M PB, 0.02%, Z-14, 0.05 grams HA.

b) From this point the assay is identical to that described in A.

A more detailed description of nucleic acid hybridization tests to detect *Legionella pneumophila* bacteria in water and liver samples is presented below.

EXAMPLE 4

Rapid Sensitive Detection of Legionella Bacteria in Water Sample: Accelerated Rate Method 1. The following components were mixed as quickly as possible and in the following order.

a) 4.5 microliters of a water sample containing about $10^5$ *Legionealla pneumophila* bacterial per ml. The number of bacteria in the water was determined at the Center of Disease Control in Atlanta by a growth test.

b) 1 microliter of the enzyme-detergent solution described in A.

c) 0.5 microliters of Legionella specific probe. The amount of probe equalled $7.5\times10^{-6}$ micrograms.

d) 10 microliters of 4.8M PB.

Assembling the hybridization mixture about 2 minutes.

2. Incubate the hybridization mixture for 36 minutes at 76° C.

3. Perform the hybridization assay as described in A. This took about 5 minutes.

4. Assay the fractions for the presence of the probe. This took about 10 minutes.

The number of Legionealla bacteria present in the hybridization mixture was about 500. This number of organisms are detected and quantitated in about one hour, from start to finish, with the use of less than $10^{-5}$ micrograms of probe. Twenty-three percent of the probe hybridized with the Legionella R-RNA in this test which was designed to be an excess probe hybridization test. Control tests were done under the same conditions, one with no bacteria added, and one with about $10^5$ *E. coli* bacteria present in the hybridization mix. In both cases only 1–2 percent of the probe behaved as if it were hybridized.

The above test can be modified to assay larger volumes for the presence of Legionella bacteria. Thus, one ml of a water sample containing $10^4$ Legionella bacteria per ml was centrifuged for 30 minutes to pellet the bacteria. A small amount of enzyme-detergent was added to the pellet and a hybridization test was performed on this mixture using the accelerated rate method and the Legionella bacteria were readily detected. Much larger volumes of sample can be centrifuged and other methods of concentrating the bacteria, including membrane filtration, can also be used. These modifications make it possible to detect a small number of bacteria in a large sample volume. Air samples can also be concentrated by methods, including membrane filtration methods, and small numbers of bacteria can be detected in large volumes of air sample.

EXAMPLE 5

Rapid Sensitive Detection of Legionella Bacteria in a Hamster Liver Sample

1. The following components were mixed as quickly as possible in the following order.

a) 4 microliters of a 10 percent liver homogenate of a hamster liver infected with *Legionealla pneumophila.* This is equivalent to 400 micrograms of liver or about $6\times10^4$ liver cells. About 750 *Legionella pneumophila* were present in this sample.

b) 4 microliters of an enzyme-detergent solution composed of: 45 milligrams/ml Proteinase K, 8% SDS, 4% sodium sarcosinate, 0.5M Tris (pH=8.2), 0.008M EDTA, 0.008M EGTA, 0.025M Nacl.

c) 4 microliters of Legionella specific probe. The quantity of probe was about $10^{-5}$ micrograms.

2. Incubate the hybridization mixture at 76° C. for 3 hours.

3. Perform the hybridization assay as described in A.

4. Assay the resulting fractions for the presence of probe hybridized to Legionella R-RNA.

The number of Legionella bacteria present in the hybridization mixture was about 750 and the amount of R-RNA present in this number of Legionella cells is about $1.1\times10^{-5}$ micrograms. The number of liver cells present was about $6\times10^4$ and the amount of liver R-RNA present was about one microgram. Ten percent of the Legionella specific probe hybridized. Control tests were done with unfected liver in the same manner and less than one percent of the probe behaved as if hybridized. Examples 4 and 5 illustrate only two of the many possible configurations for such a test. Tests utilizing different volumes, salts, detergents, probes, sample types, proteolytic enzymes, amounts of HA, incubation periods, organism types, amounts of probe, temperatures of incubation, and hybridization mate accelerating systems can be successfully utilized within the general context of the test described here. Any of the R-RNA probes can be used in a system comparable to those described above. Non R-RNA probes can also be used to good effect in these systems with some obvious modifications. For example, a test specific for a particular DNA sequence in a specific organism or group of organisms can be done exactly as described above if a step is included which converts the double strand DNA to the single strand form. In other cases different modifications of the method must be used. Bacteria such as Mycobacteria and Bacilli are difficult to break open. A step which breaks open these bacteria must then be used in conjunction with the method described above. A single incubation, in the absence of detergents, with the enzyme lysozyme, will make most Bacillus bacteria susceptible to lysis by detergents, for example. On the other hand, Mycobacteria are very difficult to lyse and may have to be physically broken open before they can be tested for.

A modification of the above method can also be used in conjunction with any transfer RNA probe or a probe specific for any other RNA present in an organism.

A step designed to concentrate small numbers of bacteria or other cells out of large volumes of samples such as air or liquid can also be used in conjunction with the hybridization test to detect most other bacterial organisms or other types of organisms.

While I have described above, in detail, the production and use of a nucleic acid probe which hybridizes only to nucleic acids from members of the Genus Legionella, it will be readily apparent to those skilled in the art from that example and the others, that other probes can be produced, based on the procedures illustrated above. Thus the method used to produce such other probes would be as follows:

1. Produce marked nucleic acid complementary to the R-RNA of a member of the group of interest.
2. Hybridize this DNA to the R-RNA from a member of the group of organisms evolutionarily most closely related to the group of organisms for which the probe is specific. Select the fraction of the marked nucleci acid which, at a specific criterion does not hybridize to R-RNA from a member of this closest related group of organisms. This fraction is specific for the organism group of interest.

Examples of these are:

a. The production of a marked probe which hybridizes only with R-RNA from a member of the bacterial Genus Leptospira and does not hybridize with R-RNA other sources.
b. The production of a marked probe which hybridizes only with R-RNA from a member of the bacterial Genus Mycoplasma and does not hybridize with R-RNA from other sources.
c. The production of a marked probe which hybridizes only with R-RNA from a member of the bacterial Family Enterbacteriaceae and does not hybridize with R-RNA from other sources.
d. The production of a marked probe which hybridizes only with R-RNA from a member of the anaerobic group of bacteria and does not hybridize with R-RNA from other sources.
e. The production of a marked probe which hybridizes only with R-RNA from a member of the group Fungi and does not hybridize with R-RNA from other sources.
f. The production of a marked probe which hybridizes only with R-RNA from any member of the Chlamydia group and does not hybridize with R-RNA from other sources.
g. The production of a marked probe which hybridizes only with R-RNA from any member of the bacterial family Mycobacteriaceae and does not hybridize with R-RNA from other sources.
h. The production of a marked probe which hybridizes R-RNA from any living organism.
i. The production of marked probe which hybridizes only with R-RNA from any mammal and does not hybridize with R-RNA from other sources.

Illustrative Embodiment of the Use of Probes for t-RNA to Detect, Quantitate and Identify Organisms t-RNA probes may be used in the same manner as the R-RNA probes to detect, identify and quantitate organisms and in some cases viruses. For example, a t-RNA probe specific for Legionealla can be produced and used in a manner similar to that described for the R-RNA probe specific only for Legionella. The illustrative embodiment described for the Legionella specific R-RNA probe thus also serves as an illustration of a t-RNA specific Legionella probe.

The genes present in many DNA and RNA viruses include t-RNA genes which are specific for the virus.

Illustrative Embodiment of the Use of Probes Specific for mRNA, hnRNA, snRNA or psRNA to: Detect, Quantitate and Identify Organisms, Cells and Viruses in Cells Probes specific for mRNA, hnRNA, snRNA or psRNA may be used in a manner alalogous to those for R-RNA and t-RNA to detect, identify and quantitate a specific large or small group of organisms, cells or viruses in cells. Since the evolutionary conservation of the individual genes which produce those various RNAs varies greatly it is possible to produce probes which will detect members of very large classes of organisms and probes which detect members of relatively small classes or organisms, cells or viruses in cells.

One example of highly conserved gene sequences are the histone genes, a family of genes present in eukaryotic cells. Histones are nuclear structural proteins which are present in all eukaryotes. The histone DNA sequences show great similarity even in widely diverged organisms. Thus, the histone genes of sea urchin and man are similar enough to hybridize together. A probe which is specific for a particular histone mRNA or for a population of histone mRNAs can detect identify the presence or absence of any member of a large group of widely diverse organisms. The sensitivity of detection of cells or organisms is enhanced by the abundance of the histone mRNAs. In order to grow, a cell or organism must synthesize histone mRNA in large amounts.

Another example invovles certain gene sequences which code for psRNA and are not conserved during evolution. Such gene sequences from one type of organism do not hybridize to DNA from distantly related species. A probe specific for one particular psRNA sequence or a population of different psRNA sequences from one organism type or virus type, can be used on detect, quantitate, and identify members of a small group of closely related organisms or a small group of closely related viruses which are in cells.

Another example is the development of a probe specific for a sequence or sequences of mRNA, hnRNA, snRNA or psRNA which can be used to examine body fluids for evidence of specific cell damage and destruction. In certain diseases cells are destroyed and their contents including cell nucleic acids are spilled into the circulating blood. Liver damage due to hepatitis is one such situation and it is known that both DNA and RNA from liver cells enters the circulating blood as a result of cell damage. A probe can be produced which is specific for an RNA sequence or sequences which are characteristic only of liver cells and are not present in other normal cell types. The existence of such RNAs is well known. This probe can then be used to detect, identify, and quantitate liver specific mRNA, hnRNA, snRNA or psRNA sequences in blood samples by nucleic acid hybridization methodology as described herein. The presence of liver damage and its extent can be determined since the amount of RNA present in the blood will reflect the extent of cell damage.

Probes specific for a particular mRNA, hnRNA, snRNA or psRNA sequence or sequences present only in a specific type of liver cell can also be produced and used to detect and quantitate the presence in the blood of the RNA sequences resulting from the damage of a specific liver cell type. Obviously the more abundant the specific RNA sequence in a liver cell the higher the sensitivity of detection of the RNA.

Damage to any body tissue or organ (including heart, kidney, brain, muscle, pancreas, spleen, etc.) may be detected and quantitated in this manner. Other body fluids including spinal fluid and urine can also be assayed for the presence of these specific RNAs.

A useful initial screening test for tissue damage from any source can be done by utilizing a probe specific for R-RNA and examining blood or other body fluids for the presence of R-RNA or t-RNA sequences. Quantitation of R-RNA or t-RNA present will provide an indication as to the extent of tissue damage without identifying the source.

Another sample of the use of the nucleic acid hybridization tests and approaches described herein is the detection and quantitation of E. coli cells containing the plasmid genes which code for the E. coli entertoxin protein. Such a test involves the use of a marked nucleic acid probe complementary to the enterotoxin protein mRNA in order to detect and quantitate the presence of E. coli bacteria containing the enterotoxin protein mRNA. This can be accomplished by utilizing the in solution hybridization methods described herein.

As discussed herein before, the use of a probe complementary to E. coli enterotoxin mRNA as a means to detect and quantitate the presence of E. coli bacterial which are producing E. coli enterotoxin and therefore contain enterotoxin mRNA, by using nucleic acid hybridization methods, has significant advantages over methods such as described in the Falkow et al. patent discussed earlier.

The same approach as described above can be utilized to detect the specific gene product of a particular microorganism which confers resistance to a particular antibiotic or other antimicrobial agent. The genes which confer resistance to most antibiotics are almost always present on plasmids in the cell. In order for an organism to produce the factor which confers resistance, the gene for the factor and the mRNA for the factor must be present in the cell. Thus a probe specific for the factor mRNA can be used to detect, identify, and quantitate the organisms which are producing the factor by utilizing nucleic acid hybridization methods.

The above examples of the use of nucleic acid probes specific for particular sequences or populations of sequences of mRNA, hnRNA, snRNA or psRNA for the purpose of detecting, identifying, and quantitating particular groups of organisms, cells, or viruses in cells containing such mRNA, hnRNA, snRNA or psRNA sequences, by nucleic acid hybridization methods, are illustrative only, and not limiting.

The Determination of the Sensitivity of Microorganisms to Antimicroorganism Agents A large number of different clinical situations require the determination of antimicrobial agent susceptibility for a variety of different bacteria and antibiotics (see "Antibiotics in Laboratory Medicine" by V. Lorian, Editor, Publisher, Williams, and Wilkens Baltimore. 1980) All of these situations utilize a method for detecting and quantitating specific classes of microorganisms. In many of these situations use of the nucleic acid hybridization tests described earlier would greatly speed up the determination of antimicrobial agent susceptibility.

As the organisms in a sample grow and divide, the amount RNA in the culture increases. A doubling of organisms results in a two fold increase in the quantity of RNA of different types which is present in the culture. Thus organism growth can be monitored by determining the quantity of RNA present in the culture at different times after the start of growth incubation. An increase in the amount of RNA present with time indicates organism growth. The magnitude of the increase indicates the extent of growth. The rate of growth is then the extent of growth per time period. Probes specific for, R-RNA, t-RNA, psR-RNA, pst-RNA, certain mRNAs or psmRNAs, certain snRNAs or pssnRNAs, or hnRNAs or pshnRNAs can be used individually or in combination to measure the growth of organisms since the quantity of each of these RNAs in a culture will increase as the organisms grow.

A culture of specific category of organisms grown in the presence of an agent or agents which completely inhibit growth will not shown an increase in RNA with time, while cultures which are partially inhibited by such agent will show a lower rate of RNA accumulation. A culture which is not inhibited will show the same rate of RNA increase as the control culture which does not contain the agent.

One example of this is in determining the susceptibility of Mycobacteria tuberculosis present in a clinical sputum sample. The first step in diagnosing such a sample is to prepare a direct smear of the sputum for staining in order to detect acid-fast bacilli. It is estimated that it requires at least $10^4-10^5$ M. tuberculosis organisms per ml of sputum to yield a positive direct smear. However, only 10 to 100 of these organisms are recoverable by growth culture methods.

If the sputum specimen shows a positive smear, the specimen is then treated to kill all bacteria except Mycobacteria, and a dilution of the treated specimen is plated on agar medium containing antimicrobial agent and on control agar which does not contain the agent. Viable individual bacteria will from colonies on the control agar while growth will be inhibited on the agar with the appropriate antimicrobial agent. The ratio of the numbers on the control agar to those on the agent treated agar is then a measure of the effectiveness of the antimicrobial agent.

A small colony will contain at least $10^6$ bacteria. This means that at least 20 divisions are needed to form a colony from one bacteria and each division will take at least 12 hours, for a total of 240 hours or 10 days, at a minimum. In most cases it takes 2–4 times this long (3 to 6 weeks) for colonies to appear.

A method described earlier for Legionella, would greatly decrease the time needed for determining antimicrobial agent susceptibility. A probe specific only for R-RNA from members of the genus Mycobacterium could be used in such a test. Such a probe would allow quantitation and a detection sensitivity equal to that described earlier for Legionella. A nucleic acid hybridization test using the accelerated hybridization rate conditions and the excess probe mode of hybridization would easily allow the detection of about 200 Mycobacteria cells. A step would be added to ensure the disruption of the Mycobacteria cells so that the R-RNA would be free to hybridize. Mycobacteria do not readily lyse in the presence of enzyme-detergent solutions.

As mentioned above, a minimum positive sputum specimen (as determined by acid staining) contains about $10^4$ to $10^5$ Mycobacteria cells per ml and these 10 to $10^2$ cells can be detected as colony forming units. For drug susceptibility studies on agar, enough Mycobacteria are added to the control and experimental agar surfaces to ensure that 40 to 50 colonies will appear on the control agar where no antimicrobial agent is present. If such a practice is followed when using a nucleic acid hybridization assay this means that the culture is started with about 50 Mycobacteria and it will then take about 3–4 cell divisions or about 2–3 days in order to obtain a detectable level of cells. If any significant inhibition of growth by the agent has occurred the control will be positive and the culture containing agent will be negative. It is clear that the use of the highly sensitive nucleic acid hybridization method can greatly reduce the time needed to determine susceptibility by 5 to 10 fold.

The above is just one example of the uses of nucleic acid hybridization test such as those described for Legionella for determining antimicrobial agent sensitivities. The sensitivity of any microorganism can be determined by utilizing a combination of the standard growth methodology and an assay for microorganisms based on nucleic acid hybridization. In addition, in many cases the specificity and sensitivity of the nucleic acid hybridization tests for microorganisms allow the determination of antibiotic sensitivity of specific organisms even in the presence of a large excess of other microorganisms or eukaryotic cells.

It is obvious that the same approach can be used to determine the presence of antimicroorganism-activity in blood, urine, other body fluids and tissues and other samples. In this case may nucleic acid hybridization procedure can be used to monitor and quantitate the effect of the blood, urine, or other sample on the growth of a specific group of microorganisms which are put into contact with said blood, urine or other samples under conditions where growth occurs if antimicrobial activity is not present.

A Method for Determining the Growth State of Cells

The overall rate of protein synthesis in a cell is determined by the number of ribosomes per cell. The rate of t-RNA synthesis is also related to the number of ribosomes per cell. Inhibition of protein synthesis in a cell results in the cessation of R-RNA synthesis by the cells. Indeed, stopping cell growth by any means results in the cessation of R-RNA synthesis and slowing cell growth results in a slowing down of R-RNA synthesis.

The newly synthesized R-RNA molecule is larger than the sum of the mature R-RNA subunits present in the ribosome. For example the R-RNA of *E. coli* is synthesized as a precursor molecule 6000 bases long. The precursor molecule is then processed to yield the R-RNA subunits (totaling about 4500 bases) which are then incorporated into ribosomes and "extra" or percursor specific R-RNA (ps R-RNA) sequences which are eventually degraded by the cell.

R-RNA is not synthesized in non-growing cells and therefore no precursor specific R-RNA sequences are present in these cells. In this case, large numbers of R-RNA molecules are present in the cell but no ps R-RNA sequences are present.

In a slowly growing cell a small amount of R-RNA precursor is synthesized and a small amount of psR-RNA is present.

In a rapidly growing cell a large amount of R-RNA precursor is synthesized and several thousand psR-RNA sequences are present.

The absence of psR-RNA in a cell signals that the cells is not growing. The ratio of R-RNA to psR-RNA in a cell is an indication of the growth rate of a cell.

Antimicrobial agents inhibit cell growth. Cells which are not growth inhibited by the agent will contain large amounts of psR-RNA. In cells which are only partially growth inhibited the psR-RNA will be present in a loer amount. The ratio of R-RNA to psR-RNA will give a measure of the degree of inhibition.

A nucleic acid probe specific for the psR-RNA sequences of a particular group of microorganisms can be used in a nucleic acid hybridization test to determine and quantitate the presence or absence of psR-RNA in those microorganisms when the organisms are grown in the presence and absence of a particular antimicroorganism agent or a group of such agents. This can be done even in the presence of large numbers of organisms which are not related to the microorganism group of interest.

It is obvious that this acid hybridization method can also be used to determine the presence of substances with antimicroorganism activity in blood, urine, other body fluids and tissues, and other samples.

This method of determining growth of cells can be used to determine the state of growth of any cell which synthesizes R-RNA. The above example is only one of many used for such a method. A method based on using a probe specific for the pst-RNA sequences of a particular group of organisms or cells can also be used to determine the state of growth of those organisms or cells.

A method based on utilizing probes specific for certain mRNAs, psmRNAs, hnRNAs, pshnRNA, snRNAs, or pssRNAs, which abundant in rapidly growing organisms or cells but absent, or present in low amount, in non-growing or slow-growing cells can also be used to determine the state of growth of these organisms or cells. For example, the mRNA for a protein, RNA polyerase, is present in abundance, several hundred copies per cell, in rapidly growing cells. In non-growing cells very little RNA is synthesized and little mRNA is present.

A method based on utilizing probe specific for certain virus mRNAs or psmRNAs which are abundant when said virus is rapidly growing in a cell and absent when the virus is present in a cell but not growing, can also be used to determine the state of growth of viruses in cells. Thus in situations where members of a particular category of organisms are known to be present in a sample it is possible to use a single probe to determine the growth state of said organisms. For example if no ps R-RNA can be detected in the organisms, they are in a non-growing state. If psR-RNA is detected in the organisms but in low amount relative to the number of organisms present, the organisms are growing slowly. If large amounts of psRNA are detected, relative to the number of organisms present, the organisms are growing rapidly.

Another approach to determining the state of growth of a particular organism or class of organisms relies in utilizing two probes, each of which will hybridize only to RNA from a particular category of organisms one probe is specific for a stable RNA (R-RNA or t-RNA) which RNA is present in said organisms in roughly the same amount in non-growing organisms or cells and rapidly growing organisms or cells; the other probe is specific for a particular mRNA, psmRNA, pst-RNA, pssnRNA, hnRNA, pshnRNA or psR-RNA sequence or sequences which RNA is present in abundance in rapidly growing cells or organisms, absent or present in low amount in non-growing organisms or cells. These probes are utilized to detect, identify, and quantitate the amounts present in the sample of the RNAs each is specific for. The ratio of the amounts of these RNAs is an indication of the growth state of the organisms or cells.

A specific example of this invovles the use of two probes, one specific for the R-RNA of members of a specific category of organisms or cells, and the other specific for the psR-RNA of the same category of organisms or cells, in order to detect, identify, and quantitate the R-RNA and psR-RNA present in a sample. The ratio of the amount of psRNA to R-RNA present in the sample is an indicator of the state of growth of the organism or cells. In rapidly growing cells there are several thousand copies of psR-RNA and the psR-RNA/R-RNA ratio is at a maximum. In slowly growing cells a relatively small amount of psR-RNA is present and the psR-RNA/R-RNA ratio is much lower. In non-growing cells psR-RNA should be absent and the psR-RNA/R-RNA ratio is at a minimum.

This same two probe method can be used with a variety of different combinations of the probes mentioned above and can be done in the presence of organisms or cells which are not members of the said specific category detected by the probe.

An obvious application of the methods described here to determine the state of growth of specific categories of organisms is the use of these methods to: determine the presence of antimicrobial agents in blood, urine, other body fluids or tissues or other samples; determine the sensitivity of specific categories of organisms to specific antimicrobial agents or groups of such agents. For example bacteria which are completely growth inhibited by a particular agent will have a minimum psR-RNA/R-RNA ratio.

Detecting, Identifying, and Quantitating Viruses

It is often important to be able to quickly determine whether a particular virus or group of viruses is present in a sample. This can be done by utilizing nucleic acid hybridization tests described herein.

The rapid nucleic acid hybridization test which combines: a) the method for rapidly making nucleic acid available for in solution hybridization; b) the method for greatly accelerating the rate of nucleic acid hybridization c) and the rapid method for assaying for the presence of a hybridized probe; is directly applicable to the detection, identification and quantitation of any group of DNA or RNA viruses present in a sample by the use of a nucleic acid probe which is complementary to the virus group of interest.

In addition, such a virus assay method could be used to determine the effectiveness of particular antiviral agents and to determine the presence of antiviral activity in blood, urine and other samples.

Method for Detecting Microorganisms Infections by Examining on Organism's Phagocytic Cells The extremely high sensitivity and specificity of detection characterizing the nucleic acid hybridization tests specific for R-RNA which have been described above, permits of a simple solution to the problem of obtaining an appropriate clinical specimen for microorganism diagnosis. A simple blood test sample which contains the white blood cell (hereinafter referred to as WBC) fraction will suffice in a large number of cases.

One manner of using this WBC approach is to first hybridize the WBC sample with a marked probe which will hybridize to R-RNA from any member of the group of all bacteria but does not hybridize to R-RNA from any other source. Such a probe serves as a general screening device for any bacteria. Samples which are positive for bacterial R-RNA are then assayed with a hierarchy of other probes in order to further identify the bacteria which is present. For example, a probe which hybridizes to R-RNA from any member of the Family Enterbacter but not to R-RNA from any other source can be used to detect or rule out Enterbacter bacteria while a probe specific only for anaerobic R-RNA would be used to detect anaerobes.

The above illustration is just one of many possible ways of using the WBCs as the primary clinical sample for the quick diagnosis of microorganism infections by nucleic acid hybridization. For example, depending on the clinical symptoms of the patient, different combinations of probes would be used in order to obtain a diagnosis.

The publications listed below are of interest in connection with various aspects of the invention and are incorporated herein as part of the disclosure.

1. Repeated Sequences in DNA R. J. Britten and D. E. Kohne, Science (1968) 161 p 529
2. Kinetics of Renaturation of DNA J. G. Wetmur and N. Davidson, J. Mol. Biol. (1968) 31 p. 349
3. Hydroxyapatite Techniques for Nucleic Acid Reassociation D. E. Kohne and R. J. Britten, in Procedures in Nucleic Acid Research (1971), eds Cantoni and Davies, Harper and Row Vol 2, p 500
4. Hybridization of Denatured RNA and Small Fragments Transferred to Nitrocellulose P. S. Thomas, Proc. Natl. Acad. Sci. USA (1980) 77 p 5201
5. DNA-DNA Hybridization on Nitrocellulose Filters: General Considerations and Non-Ideal Kinetics R. Flavell et al., Wur. J. Biochem. (1974) 47 p 535
6. Assay of DNA-RNA Hybrids of $S_1$ Nuclease Digestion and Adsorption to DEAE-Cellulose Filters I. Maxwell et al., Nucleic Acids Research (1978) 5 p 2033
7. Molecular Cloning: A Laboratory Manual T. Maniatis et al., Cold Spring Harbor Publication (1982)
8. Efficient Transcription of RNA into DNA by Avian Sarcoma Virus Polymerase J. Taylor et al., Biochemica et Biophys. Acta (1976) 442 p 324
9. Use of Specific Radioactive Probes to Stusy Transcription and Replication of the Influenze Virus Genome J. Taylor et al., J. Virology (1977) 21 #2, p 530
10. Virus Detection by Nucleic Acid Hybridization: Examination of Normal and ALs Tissue for the Presence of Poliovirus D. Kohne et al., Journal of General Virology (1981) 56 p 223–233
11. Leukemogensis by Bovine Leukemia Virus R. Kettmann et al., Proc. Natl. Acad. Sci. USA (1982) 79 #8 p 2465–2469
12. Prenatal Diagnosis of a Thalassemia: Clinical Application of Molecular Hybridization Y. Kan et al., New England Journal of Medicine (1976) 295 #21 p 1165–1167
13. Gene Deletions in a Thalassemia Prove that the 5' Locus is Functional L. Pressley et al., Proc. Natl. Acad. Sci. USA (1980) 77 #6 p 3586–3589
14. Use of Synthetic Oligonucleotides as Hybridization Probes, S. V. Suggs et al., Proc. Natl. Acad. Sci. USA (1981) 78 p 6613
15. Identification of Enterotoxigenic *E. coli* by Colony Hybridization Using 3 Enterotoxin Gene Probes S. L. Mosely et al. J. of Infect. Diseases (1982) 145 #6 p 863
16. DNA Reassociation in the Taxonomy of Enteric Bacteria D. Brenner, Int. J. Systematic Bacteriology (1973) 23 #4 p 298–307
17. Comparative study of Ribosomal RNA Cistrons in Enterobacteria and Myxobacteria R. Moore et al., J. Bacteriology (1967) 94 p 1066–1074
18. Ribosomal RNA Similarities in the Classification of Rhodococcus and Related Taxa M. Mordarski et al., J. General Microbiology (1980) 118 p. 313–319
19. Retention of Common Nucleotide Sequences in the Ribosomal RNA DNA of Eukaryotes and Some of their Physical Characteristics J. Sinclair et al., Biochemistry (1971) 10 p 2761
20. Homologies Among Ribosomal RNA and Messenger RNA Genes in Chloroplasts, Mitochondria and *E. coli* H. Bohnert et al., Molecular and General Genetics (1980) 179 p 539–545

21. Heterogeneity of the Conserved Ribosomal RNA Sequences of *Bacillus subtilis* R. Doe et al., J. Bacteriology (1966) 92 #1 p 88
22. Isolation and Characterization of Bacterial Ribosomal RNA Cistrons D. Kohne, Biophysical Journal (1968) 8 #10 p 1104–1118
23. Taxonomic Relations Between Archaebacteria Including 6 Novel Genera Examined by Cross Hybridization of DNAs and 16S R-RNAs J. Tu et al., J. Mol. Evol. (1982) 18 p 109
24. R-RNA Cistron Homologies Among Hypohomicrobium and Various Other Bacteria, R. Moore, Canadian J. Microbiology (1977) 23 p 478
25. Conservation of Transfer RNA and 5S RNA Cistrons in Enterobacteriaceae D. J. Brenner et al., J. Bacteriology Vol 129 #3 (March 1977) p 1435
26. Sequence Homology of Mitochondrial Leucul-tNA Cistron in Different Organisms S. Jakovcic et al., Biochemistry Vol. 14 #10 (May 20, 1975), p. 2037
27. Synthetic Deoxyoligonucleotides as General Probes for Chloroplast t-RNA Genes J. A. Nickoloff and R. B. Hallick, Nucleci Acids Research, Vol. 10 #24 (1982) p 8191–8210
28. Antibiotics in Laboratory Medicine V. Lorian ed. Williams and Wilkens (Baltimore/London) 1980
29. Diagnostic Microbiology Finegold and Martin, Editors, C. V. Mosby Co. (St. Louis) 1982
30. Spotblot: A Hybridization Assay for Specific DNA Sequences in Multiple Samples M. Cunningham, Analytical Biochemistry Vol. 128 (1983) p. 415
31. (29) Analysis of Repeating DNA Sequences by Reassociation R. Britten et al., in: Methods in Enzumology XXIX, page 363, Eds. Grossman and Moldave, Academic Press, New York (1974)
32. Studies on Nucleic Acid Reassociation Kinetics: Retarded Rate of Hybridization of RNA with Excess DNA G. Galau et al., Proc. Natl. Acad. Sci. USA Vol. 74 #6 (1974) p 2306
33. Acceleration of DNA Renaturation Rates J. Wetmur, Biopolymers Vol. 14 (1975) p 2517
34. Room Temperature Method for Increasing the Rate of DNA Reassociation by Many Thousandfold: The Phenol Emulsion Reassociation Technique D. Kohne et al., Biochemistry Vol. 16 #24 (1977) p 5349
35. Molecular Biology D. Feifelder, Science Books International (Boston) Van Nostrand Reinhold Co. (New York) 1983
36. Gene Expression 2 B. Lewin, J. Wiley & Sons, Wiley-Interscience Publication (1980) New York
37. Gene Expression 1 B. Lewin, J. Wiley & Sons, Wiley-Interscience Publication (1974) New York As used in the specification and claims the following terms are definited as follows:

| DEFINITION OF TERMS | |
|---|---|
| base (see nucleotide) | |
| base pair mismatches (see imperfectly complementary base sequence) | |
| base seqeunce (nucleotide sequence or gene sequence or polynucleotide sequence or single strand nucleic acid sequence) | A DNA or RNA molecule consisting of multiple bases. |
| complementary base pairs | Certain of the bases have a chemical affinity for each other and pair together, or are complementary to one another. The complementary base pairs are A:T and G:C in DNA and A:U in RNA. |
| complementary strands or complementary base sequences | perfectly complementary nucleic acid molecules are nucleic acid molecules in which each base in one molecule is paired with its complementary base in the other strand, to form a stable helical double strand molecule. The individual strands are termed complementary strands. |
| criterion | Most preciesely defined as the difference between the temperature of melting of the double strand nucleic acid and the temperature at which hybridization is done. The melting temperature of a double strand nucleic acid is determined primarily by the salt concentration of the solution. The criterion determines the degree of complementarity needed for two single strands to form a stable double strand molecules. The criterion can be described as highly stringent, or not very stringent. A highly stringent criterion requires that two |

-continued

DEFINITION OF TERMS

| | |
|---|---|
| | interacting complementary sequences be highly complementary in sequence in order to form a stable double strand molecule. A poorly stringent criterion is one which allows relatively dissimilar complimentary strands to interact and form a double strand molecule. High stringency allows the presence of only a small fraction of base pair mismatches in a double strand molecule. A poorly stringent criterion allows a much larger fraction of base pair mismatches in the hybridization product. |
| denatured or dissociated nucleic acid | The bond between the paired bases in a double strand nucleic acid molecule can be broken, resulting in two single strand molecules, which then diffuse away from each other. |
| double strand nucleic acid | As it is found in the cell, most DNA is in the double strand-state. The DNA is made up of two DNA molecules or strands wound helically around each other. The bases face inward and each base is specifically bonded to a complementary base in the other strand. For example, an A in one strand is always paired with a T in the other strand, while a G in one strand is paired with a C in the other strand. In a bacterial cell the double strand molecule is about $5 \times 10^6$ base pairs long. Each of the bases in one strand of this molecule is paired with its base complement in the other strand. The base sequences of the individual double strand molecules are termed complementary strands. |
| hybridition (see nucleic and hybridization) | |
| imperfectly complementary base sequences (base pair mismatches) | Stable double strand molecules can be formed between two strands where a fraction of the bases in the one strand are paired with a non-complementary base in the other strand. |
| marked probe or marked sequence | Single strand nucleic acid molecules which are used to detect the presence of other nucleic acids by the process of nucleic acid hybridization. The probe molecules are marked so that they can be specifically detected. This is done by incorporating a specific marker molecule into the nucleic acid or by attaching a specific marker to the nucleic acid. The most effective probes are marked, single strand sequences, which cannot self hybridize but can hybridize only if the nucleic acid to be detected is present. A large number of different markers are available. These include radioactive and fluorescent molecules. |
| nucleic acid hybridization or hybridization (reassociation, or renaturation) | The bond between the two strands of a double strand molecule can be broken and the two single strands can be completely separated from each other. Under the proper conditions the complementary single strands can collide, recognize each other and reform the double strand helical molecule. This process of formation of double strand molecules from complementary |

DEFINITION OF TERMS

| | |
|---|---|
| | single strand molecules is called nucleic acid hybridization. Nucleic acid hybridization also occurs between partially complementary single strands of RNA and DNA. |
| nucleotide, nucleotide base or base | Most DNA consists of sequences of only four nitrogeneous bases: adenine (A), thymine (T), guanine (G), and cytosine (C). Together these bases form the genetic alphabet, and long ordered sequences of them contain, in coded form, much of the information present in genes. Most RNA also consists of sequences of only four bases. However, in RNA, thymine is replaced by uridine (U). |
| reassociation | (see nucleic acid hybridization) |
| renaturation | (see nucleic acid hybridization) |
| ribosomal RNA or R-RNA | The RNA which is present in ribosomes. Virtually all ribosomes contain 3 single strand RNA subunits: one large, one medium-sized, and one small. |
| ribosome | A cellular particle (containing RNA and protein) necessary for protein synthesis. All life forms except viruses contain ribosomes. |
| R-RNA DNA or R-RNA gene | The base sequence in the DNA which codes for ribosomal RNA. Each R-RNA subunit is coded for by a separate gene. |
| R-RNA probe | A marked nucleic acid sequence which is complementary to R-RNA and therefore will hybridize with R-RNA to form a stable double strand molecule. |
| mRNA | Each individual mRNA is a direct gene product containing the information necessary to specify a particular protein. The machinery of the cell translates the sequence of the mRNA into a specific protein. Many different mRNAs exist in each cell. |
| hnRNA | A complex class of RNA sequences presence in the nucleus of eukaryotic cells which includes precursor mRNA molecules. Most hnRNA sequences never leave the nucleus. The function of most of these molecules in unknown. |
| snRNA | A class of relatively stable small nuclear RNA molecules which present primarily in the nucleus of eukaryotic cells in large numbers. |
| precursor RNA | Many RNA molecules in both prokaryotes and eukaryotes are synthesized as part of a large RNA molecules which is then processed to yield mature RNA molecules of various types and other smaller sequences which are apparently discarded. |
| precursor specific RNA (ps RNA) | The RNA sequences present in precursor mRNA, t-RNA, R-RNA, snRNA and hnRNA which are not present in the mature R-RNA, t-RNA, mRNA, snRNA, and hnRNA molecules. |
| thermal stability of double strand nucleic acid molecules | The thermal stability or melting temperature at which half of a population of double strand molecules has been converted to the single strand form. |
| restriction enzymes | Components of the restriction-modification cellular defense system against foreign nucleic acids. These enzymes cut unmodified (e.g., methylated) double-stranded DNA at specific |

| DEFINITION OF TERMS | |
|---|---|
| | sequences which exhibition twofold symmetry about a point. |
| transfer RNA (t-RNA) | During protein synthesis individual amino acids are aligned in the proper order by various specific adaptor molecules or t-RNA molecules. Each amino acid is ordered by a different t-RNA species. |

While the invention has been described and illustrated in detail, it will be apparent to those skilled in the art that various changes, equivalents and alternatives may be resorted to without departing from the spirit of the invention, and all of such changes, equivalents and alternatives are contemplated as may come within the scope of the appended claims and equivalents thereof.

What is claimed is:

1. A method for determining the sensitivity of a microorganism or group of microorganisms to at least one antimicrobial agent, said method comprising the steps of:
    (a) providing at least one antimicrobial agent to a first sample, said first sample containing a microorganism or microorganisms belonging to a group of microorganisms;
    (b) incubating said first sample for a predetermined period of time under growth conditions; and
    (c) assaying said first sample with at least one probe to determine the presence and amount of ribosomal nucleic acid specific to said microorganism or group of microorganisms,
    wherein said probe contains a nucleic acid molecule which hybridizes with only a subunit subsequence of said ribosomal nucleic acid under hybridization conditions,
    wherein said probe and said first sample are incubated under said hybridization conditions, such that said nucleic acid molecule hybridizes with the subsequence of said ribosomal nucleic acid, and said probe does not hybridize with any sequence which will prevent specific detection of said microorganism or microorganisms under said hybridization conditions, and
    wherein the presence and amount of said ribosomal nucleic acid present in said first sample is an indication of the state of growth of said microorganism or microorganisms, said state of growth being an indication of the sensitivity of said microorganism or group of microorganisms to said agent.

2. The method of claim 1, wherein said ribosomal nucleic acid is rRNA.

3. The method of claim 1, wherein said ribosomal nucleic acid is genomic rRNA.

4. The method of claim 1, wherein the microorganisms belonging to said group of microorganisms belong to a taxon selected from the group consisting of species, genus, family, order, class, phylum and kingdom.

5. The method of claim 1, wherein said probe has a label.

6. The method of claim 5, wherein said label is selected from the group consisting of a radioisotope, a fluor, an enzyme and biotin.

7. The method of claim 1, wherein said first sample contains a bodily fluid or tissue.

8. The method of claim 1, wherein said first sample contains a bodily fluid consisting of blood or urine.

9. The method of claim 1, further comprising the step of:
    comparing the state of growth of said microorganism or microorganisms in said first sample with the state of growth of said microorganism or microorganisms in a second sample as a further indication of the sensitivity of said microorganism or group of microorganisms to said agent, said second sample being incubated in the absence of said agent for said predetermined period of time under said growth conditions.

10. The method of claim 9, wherein said first and second samples have the same source.

11. The method of claim 10, wherein said first and second samples contain a bodily fluid or tissue.

12. The method of claim 10, wherein said first and second samples contain a bodily fluid consisting of blood or urine.

13. The method of claim 1, further comprising the steps of:
    assaying said first sample with said probe prior to step (a) to determine the presence and amount of said ribosomal nucleic acid; and
    comparing the amounts of said ribosomal nucleic acid present in said first sample in each said assaying step, wherein the relative amounts of said ribosomal nucleic acid present in said first sample in said assaying steps are a further indication of the state of growth of said microorganism or microorganisms.

14. The method of claim 13, wherein said ribosomal nucleic acid is rRNA.

15. The method of claim 13, wherein said ribosomal nucleic acid is genomic rRNA.

16. The method of claim 13, wherein the microorganisms belonging to said group of microorganisms belong to a taxon selected from the group consisting of species, genus, family, order, class, phylum and kingdom.

17. The method of claim 13, wherein said probe has a label.

18. The method of claim 17, wherein said label is selected from the group consisting of a radioisotope, a fluor, an enzyme and biotin.

19. The method of claim 13, wherein said first sample contains a bodily fluid or tissue.

20. The method of claim 13, wherein said first sample contains a bodily fluid consisting of blood or urine.

21. The method of claim 13, further comprising the step of:
    comparing the state of growth of said microorganism or microorganisms in said first sample with the state of growth of said microorganism or microorganisms in a second sample as a further indication of the sensitivity of said microorganism or group of microorganisms to said agent, said second sample being incubated in the absence of said agent for said predetermined period of time under said growth conditions.

22. The method of claim 21, wherein said first and second samples have the same source.

23. The method of claim 22, wherein said first and second samples contain a bodily fluid or tissue.

24. The method of claim 23, wherein said first and second samples contain a bodily fluid consisting of blood or urine.

25. A method for determining the sensitivity of a microorganism or group of microorganisms to at least one antimicrobial agent, said method comprising the steps of:

(a) providing at least one antimicrobial agent to a first sample, said first sample containing a microorganism or microorganisms belonging to a group of microorganisms;

(b) incubating said first sample for a predetermined period of time under growth conditions;

(c) removing at least two sample aliquots of said first sample during said predetermined period of time, wherein each of said sample aliquots is removed at a different time, and wherein one of said sample aliquots is removed at the beginning of said predetermined period of time and another of said sample aliquots is removed at the end of said predetermined period of time;

(d) assaying each of said sample aliquots with at least one probe to determine the amount of ribosomal nucleic acid specific to said microorganism or group of microorganisms in each of said sample aliquots;

wherein said probe contains a nucleic acid molecule which hybridizes with only a subunit subsequence of said ribosomal nucleic acid under hybridization conditions, wherein said probe and each of said sample aliquots is incubated under said hybridization conditions, such that said nucleic acid molecule hybridizes with the subsequence of said ribosomal nucleic acid, and said probe does not hybridize with any sequence which will prevent specific detection of said microorganism or microorganisms under said hybridization conditions; and (e) comparing the amounts of said ribosomal nucleic acid present in each of said sample aliquots, wherein the relative amounts of said ribosomal nucleic acid present in said sample aliquots are an indication of the state of growth of said microorganism or microorganisms over said predetermined period of time, said state of growth being an indication of the sensitivity of said microorganism or group or microorganisms to said agent.

26. The method of claim 25, wherein said ribosomal nucleic acid is rRNA.

27. The method of claim 25, wherein said ribosomal nucleic acid is genomic rRNA.

28. The method of claim 25, wherein said probe has a label.

29. The method of claim 28, wherein said label is selected from the group consisting of a radioisotope, a fluor, an enzyme and biotin.

30. The method of claim 25, wherein said first sample contains a bodily fluid or tissue.

31. The method of claim 25, wherein said first sample contains a bodily fluid consisting of blood or urine.

32. The method of claim 25, further comprising the step of:

comparing the state of growth of said microorganism or microorganisms in said first sample with the state of growth of said microorganism or microorganisms in a second sample as a further indication of the sensitivity of said microorganism or group of microorganisms to said agent over said predetermined period of time, said second sample being incubated in the absence of said agent for said predetermined period of time under said growth conditions.

33. The method of claim 32, wherein said first and second samples have the same source.

34. The method of claim 33, wherein said first and second samples contain a bodily fluid or tissue.

35. The method of claim 33, wherein said first and second samples contain a bodily fluid consisting of blood or urine.

36. The method of claim 32, further comprising the steps of:

removing an aliquot of said second sample at each said different time;

assaying each said aliquot of said second sample with said probe to determine the amount of said ribosomal nucleic acid in each said aliquot of said second sample; and comparing the amounts of said ribosomal nucleic acid present in each said aliquot of said first and second samples at each said different time, wherein the relative amounts of said ribosomal nucleic acid present in said aliquots of said first and second samples at each said different time are a further indication of the state of growth of said microorganism or microorganisms over said predetermined period of time.

37. The method of claim 25, further comprising the steps of:

assaying a first aliquot of said first sample with said probe before step (a) to determine the presence and amount of said ribosomal nucleic acid; and comparing the amounts of said ribosomal nucleic acid present in said first aliquot and said sample aliquots, wherein the relative amounts of said ribosomal nucleic acid present in said first aliquot and said sample aliquots at each said different time are a further indication of the state of growth of said microorganism or microorganisms over said predetermined period of time.

38. The method of claim 37, further comprising the step of:

comparing the state of growth of said microorganism or microorganisms in said first sample with the state of growth of said microorganism or microorganisms in a second sample as a further indication of the sensitivity of said microorganism or group of microorganisms to said agent, said second sample being incubated in the absence of said agent for said predetermined period of time under said growth conditions.

39. The method of claim 38, wherein said first and second samples have the same source.

40. The method of claim 39, wherein said first and second samples contain a bodily fluid or tissue.

41. The method of claim 39, wherein said first and second samples contain a bodily fluid consisting of blood or urine.

42. The method of claim 38, further comprising the steps of:

removing an aliquot of said second sample at each said different time;

assaying each said aliquot of said second sample with said probe to determine the presence and amount of said ribosomal nucleic acid; and comparing the amounts of said ribosomal nucleic acid present in each said aliquot of said first and second samples at each said different time, wherein the relative amounts of said ribosomal nucleic acid present in said aliquots of said first and second samples at each said different time are a further indication of the state of growth of said microorganism or microorganisms over said predetermined period of time.

43. A method for determining the sensitivity of a microorganism or group of microorganisms to at least one antimicrobial agent, said microorganism or microorganisms belonging to said group of microorganisms being present in a subject, said method comprising the steps of:

(a) treating a subject with at least one antimicrobial agent, said subject having a microorganism or microorganisms belonging to a group of microorganisms;

(b) removing one or more samples from said subject, said samples being removed at different times following step (a);

(c) assaying said samples with at least one probe to determine the presence and amount of ribosomal nucleic acid specific to said microorganism or group of microorganisms at said different times, wherein said probe contains a nucleic acid molecule which hybridizes with only a subunit subsequence of said ribosomal nucleic acid under hybridization conditions, wherein said probe and said samples are incubated under said hybridization conditions, such that said nucleic acid molecule hybridizes with the subsequence of said ribosomal nucleic acid, and said probe does not hybridize with any sequence which will prevent specific detection of said microorganism or microorganisms under said hybridization conditions; and (d) comparing the amounts of said ribosomal nucleic acid present in said samples, wherein the relative amounts of said ribosomal nucleic acid present in said samples is an indication of the state of growth of said microorganism or microorganisms over said different times, said state of growth being an indication of the sensitivity of said microorganism or group of microorganisms to said agent.

44. The method of claim 43, wherein said subject is an animal.

45. The method of claim 44, wherein said animal is human.

46. The method of claim 43, wherein said ribosomal nucleic acid of said samples is rRNA.

47. The method of claim 43, wherein said ribosomal nucleic acid of said samples is genomic rRNA.

48. The method of claim 43, wherein the microorganisms belonging to said group of microorganisms belong to a taxon selected from the group consisting of species, genus, family, order, class, phylum and kingdom.

49. The method of claim 43, wherein said probe has a label.

50. The method of claim 49, wherein said label is selected from the group consisting of a radioisotope, a fluor, an enzyme and biotin.

51. The method of claim 43, wherein said samples contain a bodily fluid or tissue.

52. The method of claim 43, wherein said samples contain a bodily fluid consisting of blood or urine.

53. The method of claim 43, further comprising the steps of:

removing a first sample from said subject before step (a);

assaying said first sample with said probe to determine the presence and amount of said ribosomal nucleic acid; and comparing the amounts of said ribosomal nucleic acid present in said first sample and said samples, wherein the relative amounts of said ribosomal nucleic acid present in said first sample and said samples are a further indication of the state of growth of said microorganism or microorganisms over said different times.

54. The method of claim 53, wherein said subject is an animal.

55. The method of claim 54, wherein said subject is an human.

56. The method of claim 53, wherein said ribosomal nucleic acid of said first sample and said samples is rRNA.

57. The method of claim 53, wherein said ribosomal nucleic acid of said first sample and said samples is genomic rRNA.

58. The method of claim 53, wherein the microorganisms belonging to said group of microorganisms belong to a taxon selected from the group consisting of species, genus, family, order, class, phylum and kingdom.

59. The method of claim 53, wherein said probe has a label.

60. The method of claim 59, wherein said label is selected from the group consisting of a radioisotope, a fluor, an enzyme and biotin.

61. The method of claim 53, wherein said first sample and said samples contain a bodily fluid or tissue.

62. The method of claim 53, wherein said first sample and said samples contain a bodily fluid consisting of blood or urine.

* * * * *